US008367101B2

(12) United States Patent
McAllister et al.

(10) Patent No.: US 8,367,101 B2
(45) Date of Patent: Feb. 5, 2013

(54) PHARMACEUTICAL FORMULATION

(75) Inventors: Stephen Mark McAllister, Harlow (GB); Ronald K. Raby, Jr., Collegeville, PA (US); Adrian Brown, Harlow (GB); Allan J. Clarke, Collegeville, PA (US); Daniel N. Margetson, Harlow (GB); Wayne Matthews, Harlow (GB)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 10/060,849

(22) Filed: Jan. 30, 2002

(65) Prior Publication Data

US 2003/0068369 A1    Apr. 10, 2003

(30) Foreign Application Priority Data

Jan. 30, 2001    (GB) .................................. 0102342.3

(51) Int. Cl.
*A61K 9/48* (2006.01)
*A61K 9/52* (2006.01)
*A61K 9/58* (2006.01)
*A61K 9/62* (2006.01)

(52) U.S. Cl. ........ 424/451; 424/452; 424/457; 424/461; 424/462

(58) Field of Classification Search .................. 424/451, 424/472, 400
See application file for complete search history.

(56) References Cited

U.S. PATENT DOCUMENTS

| 3,186,910 A | 6/1965 | Glassman |
| 3,228,789 A | 1/1966 | Glassman |
| 3,314,809 A * | 4/1967 | Klug ......................... 106/194.1 |
| 3,394,983 A | 7/1968 | Greif et al. |
| 3,399,803 A | 9/1968 | Oglevee et al. |
| 3,723,312 A | 3/1973 | Hay, Jr. |
| 3,779,942 A * | 12/1973 | Bolles ......................... 428/402.2 |
| 4,196,565 A | 4/1980 | Bodenmann et al. |
| 4,250,097 A | 2/1981 | Pfister |
| 4,281,763 A | 8/1981 | Pace |
| 4,351,825 A | 9/1982 | Sothmann et al. |
| 4,417,591 A | 11/1983 | Culver |
| 4,483,846 A | 11/1984 | Koide et al. |
| 4,487,327 A | 12/1984 | Grayson |
| 4,498,080 A | 2/1985 | Culver |
| 4,543,138 A | 9/1985 | Bollinger et al. |
| 4,550,238 A | 10/1985 | Van Herle et al. |
| 4,557,180 A | 12/1985 | Glomeau |
| 4,564,363 A | 1/1986 | Bagnall et al. |
| 4,576,284 A | 3/1986 | Wittwer |
| 4,591,475 A | 5/1986 | Tomka et al. |
| D285,837 S | 9/1986 | Wittwer |
| 4,625,513 A | 12/1986 | Glomeau |
| 4,655,840 A | 4/1987 | Wittwer et al. |
| 4,673,438 A | 6/1987 | Wittwer et al. |
| 4,678,516 A | 7/1987 | Alderman et al. |
| 4,696,163 A | 9/1987 | Glomeau |
| 4,705,695 A | 11/1987 | Lehmann et al. |
| 4,724,019 A | 2/1988 | Brown et al. |
| 4,737,357 A | 4/1988 | Lehmann et al. |
| 4,738,724 A | 4/1988 | Wittwer et al. |
| 4,738,817 A | 4/1988 | Wittwer et al. |
| 4,764,378 A | 8/1988 | Keith et al. |
| 4,766,728 A | 8/1988 | Glomeau |
| 4,790,881 A | 12/1988 | Wittwer et al. |
| 4,792,451 A | 12/1988 | Kim |
| 4,793,493 A | 12/1988 | Makiej et al. |
| 4,795,644 A | 1/1989 | Zentner |
| 4,806,337 A | 2/1989 | Snipes et al. |
| 4,833,221 A | 5/1989 | Albrecht et al. |
| 4,892,741 A | 1/1990 | Ohm et al. |
| 4,899,516 A | 2/1990 | Krieger et al. |
| 4,928,840 A | 5/1990 | Barshay et al. |
| 4,936,461 A | 6/1990 | Makiej et al. |
| 4,964,262 A | 10/1990 | Moser et al. |
| 5,004,601 A | 4/1991 | Snipes |
| 5,074,426 A | 12/1991 | Goodhart et al. |
| 5,082,655 A | 1/1992 | Snipes et al. |
| 5,085,033 A | 2/1992 | Graham |
| 5,110,877 A | 5/1992 | Hoess et al. |
| 5,135,752 A | 8/1992 | Snipes |
| 5,139,790 A | 8/1992 | Snipes |
| 5,155,172 A | 10/1992 | Siol et al. |
| 5,219,931 A | 6/1993 | Siol et al. |
| 5,225,202 A | 7/1993 | Hodges et al. |
| 5,236,689 A | 8/1993 | Wong et al. |

(Continued)

FOREIGN PATENT DOCUMENTS

| BE | 900950 | 4/1985 |
| DE | 3524963 | 1/1987 |

(Continued)

OTHER PUBLICATIONS

Handbook of Pharmaceutical Excipients, p. 207-208, 1986.*
Lamprecht et al. "FK506 Microparticles Mitigate Experimental Colitis with Minor Renal Calcineurin Suppression", Pharmaceutical Research, vol. 22, No. 2, Feb. 2005; pp. 193-196.*
Hu et al., "Characterization of Norfloxacine Release from Tablet Coasted with a New pH Sensitive Polymer, P-4135F", Journal of Drug Targeting, 1999, vol. 7, No. 3, pp. 223-232.
U.S. Appl. No. 10/470,438—Office Action.
U.S. Appl. No. 10/470,439—Office Action.
U.S. Appl. No. 10/060,603—Office Action.

(Continued)

*Primary Examiner* — Susan Tran
(74) *Attorney, Agent, or Firm* — Finnegan, Henderson, Farabow, Garrett & Dunner, LLP

(57) ABSTRACT

The present invention is directed to pharmaceutically acceptable polymeric compositions suitable for injection molding of single or multi-component pharmaceutical dosage forms comprising a plurality of drug substance containing sub-units, being capsule compartments and/or solid sub-units comprising a solid matrix of a polymer which contains a drug substance, the sub-units being connected together in the assembled dosage form by a weld between parts of the assembled dosage form.

4 Claims, 13 Drawing Sheets

U.S. PATENT DOCUMENTS

| | | | |
|---|---|---|---|
| RE34,390 E | 9/1993 | Culver | |
| 5,244,668 A | 9/1993 | Snipes | |
| 5,270,397 A | 12/1993 | Rhein et al. | |
| 5,280,073 A | 1/1994 | Siol et al. | |
| 5,312,008 A | 5/1994 | Davis | |
| 5,312,388 A | 5/1994 | Wong et al. | |
| 5,387,421 A | 2/1995 | Amidon et al. | |
| 5,443,461 A | 8/1995 | Atkinson et al. | |
| 5,456,919 A | 10/1995 | Patell et al. | |
| 5,489,436 A | 2/1996 | Hoy et al. | |
| 5,548,033 A | 8/1996 | Vetter et al. | |
| 5,644,011 A * | 7/1997 | Lehmann et al. | 526/319 |
| 5,652,316 A | 7/1997 | May et al. | |
| 5,672,359 A | 9/1997 | Digenis et al. | |
| 5,674,530 A | 10/1997 | Crison et al. | |
| 5,705,189 A * | 1/1998 | Lehmann et al. | 424/451 |
| 5,750,143 A | 5/1998 | Rashid et al. | |
| 5,769,267 A | 6/1998 | Duynslager et al. | |
| 5,770,224 A | 6/1998 | Rashid et al. | |
| 5,837,780 A | 11/1998 | Albrecht et al. | |
| 5,861,173 A | 1/1999 | Nishioka et al. | |
| 5,976,571 A | 11/1999 | Crison et al. | |
| 6,139,875 A * | 10/2000 | Adams et al. | 424/476 |
| 6,200,600 B1 | 3/2001 | Rashid | |
| 6,207,191 B1 | 3/2001 | Crison et al. | |
| 6,284,803 B1 | 9/2001 | Kothrade et al. | |
| 6,287,470 B1 | 9/2001 | Vetter et al. | |
| 6,309,666 B1 * | 10/2001 | Hatano et al. | 424/463 |
| 6,318,650 B1 | 11/2001 | Breitenbach et al. | |
| 6,355,712 B1 | 3/2002 | Schultes et al. | |
| 6,367,228 B1 | 4/2002 | Wurst et al. | |
| 6,368,629 B1 | 4/2002 | Watanabe et al. | |
| 6,548,513 B1 | 4/2003 | Creekmore et al. | |
| 6,551,617 B1 | 4/2003 | Corbo et al. | |
| D481,456 S | 10/2003 | McAllister et al. | |
| D493,518 S | 7/2004 | McAllister et al. | |
| 6,765,046 B1 | 7/2004 | Numrich et al. | |
| 6,890,993 B2 | 5/2005 | Schultes et al. | |
| 7,014,810 B2 | 3/2006 | Krull et al. | |
| 7,217,381 B2 | 5/2007 | Sowden | |
| 2001/0008637 A1 | 7/2001 | Hochrainer et al. | |
| 2002/0160042 A1* | 10/2002 | Petereit et al. | 424/464 |
| 2003/0029558 A1 | 2/2003 | Hochrainer et al. | |
| 2003/0049311 A1 | 3/2003 | McAllister et al. | |
| 2003/0068369 A1 | 4/2003 | McAllister et al. | |
| 2003/0194428 A1 | 10/2003 | Miller et al. | |
| 2003/0194429 A1 | 10/2003 | Miller et al. | |
| 2003/0194430 A1 | 10/2003 | Miller et al. | |
| 2003/0194431 A1 | 10/2003 | Miller et al. | |
| 2003/0224050 A1* | 12/2003 | Chiao et al. | 424/471 |
| 2004/0115256 A1 | 6/2004 | MacAllister et al. | |
| 2004/0131668 A1 | 7/2004 | Hochrainer et al. | |
| 2004/0166153 A1 | 8/2004 | McAllister et al. | |
| 2005/0008690 A1 | 1/2005 | Miller et al. | |
| 2005/0080188 A1 | 4/2005 | Schultes et al. | |
| 2005/0142203 A1* | 6/2005 | Heinicke | 424/489 |
| 2005/0267250 A1 | 12/2005 | Theil et al. | |
| 2006/0052515 A1 | 3/2006 | Schultes et al. | |
| 2006/0121248 A1 | 6/2006 | Lorenz et al. | |
| 2006/0147714 A1 | 7/2006 | Schultes et al. | |
| 2007/0055017 A1 | 3/2007 | Schultes et al. | |
| 2007/0066708 A1 | 3/2007 | Goldacker et al. | |
| 2007/0112135 A1 | 5/2007 | Wicker et al. | |
| 2007/0122624 A1 | 5/2007 | Schultes et al. | |
| 2007/0123610 A1 | 5/2007 | Schultes et al. | |
| 2007/0222117 A1 | 9/2007 | Hoess et al. | |
| 2007/0276093 A1 | 11/2007 | Schultes et al. | |
| 2008/0014257 A1* | 1/2008 | He et al. | 424/457 |

FOREIGN PATENT DOCUMENTS

| | | |
|---|---|---|
| DE | 3727894 | 7/1990 |
| EP | 141397 | 10/1984 |
| EP | 0 211 079 | 1/1985 |
| EP | 143524 | 6/1985 |
| EP | 0 228 067 | 12/1986 |
| EP | 0 364 060 | 4/1990 |
| EP | 0410422 | 1/1991 |
| EP | 0 759 303 | 2/1997 |
| EP | 0759303 | 2/1997 |
| EP | 1266655 A | 12/2002 |
| FR | 2524311 | 4/1982 |
| GB | 1496737 | 6/1975 |
| GB | 2172569 | 3/1985 |
| GB | 2187703 | 3/1987 |
| JP | 11-322584 | 11/1999 |
| JP | 2003 171277 | 6/2003 |
| NL | 7610038 | 9/1976 |
| WO | WO 90/12567 | 11/1990 |
| WO | WO 92/13521 | 8/1992 |
| WO | WO 94/09743 | 5/1994 |
| WO | WO 95/13056 | 5/1995 |
| WO | 95/16438 | 6/1995 |
| WO | WO 95/16438 | 6/1995 |
| WO | 96/15775 | 5/1996 |
| WO | 96/24337 | 8/1996 |
| WO | 97/33569 | 9/1997 |
| WO | WO 01/08666 | 2/2001 |
| WO | WO 01/39751 | 6/2001 |
| WO | WO 01/43935 | 6/2001 |
| WO | WO 02/098625 | 12/2002 |
| WO | WO 03/043601 | 5/2003 |
| WO | WO 2004/010978 | 2/2004 |
| WO | 2005/070401 | 8/2005 |
| WO | 2006/107593 | 10/2006 |

OTHER PUBLICATIONS

Fukui et al., Int. J. Pharm vol. 217, 2001, pp. 33-43.
Meyuys et al., Euro J. Pharm. Sci., vol. 24, 2005, pp. 207-212.
Nakamichi et al., J. Drug Delivery Sci & Tech. vol. 14, No. 3, pp. 193-198 (2004).
Kohri et al., Int. J. Pharm 49(3): 213-221 (1989).

* cited by examiner

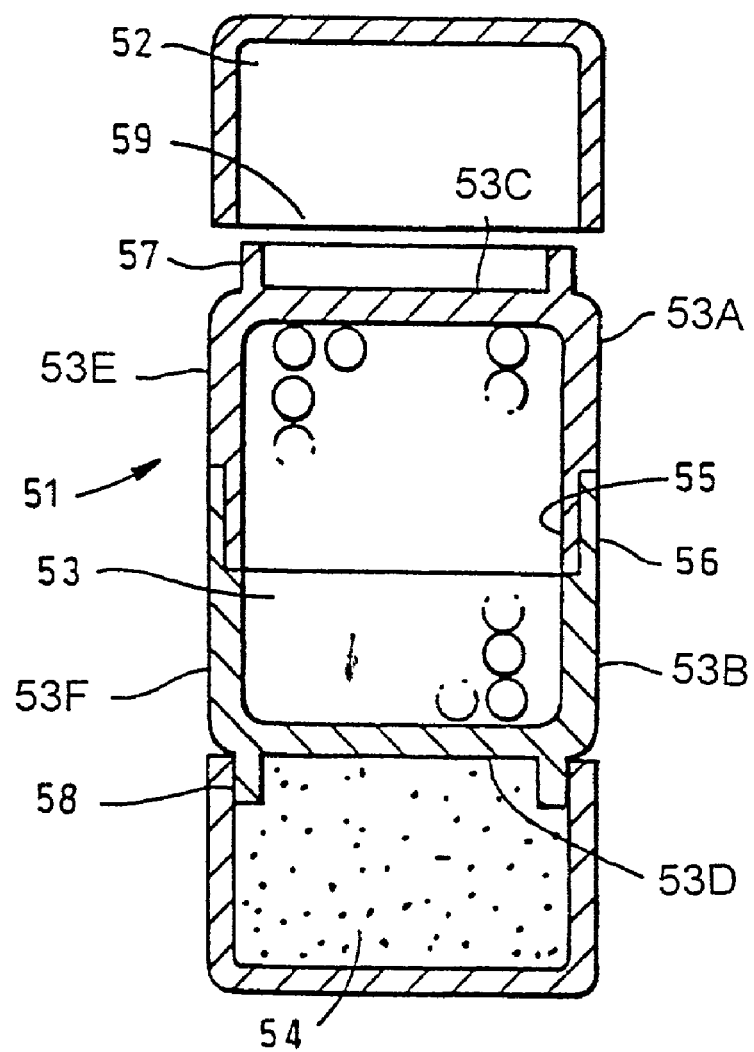

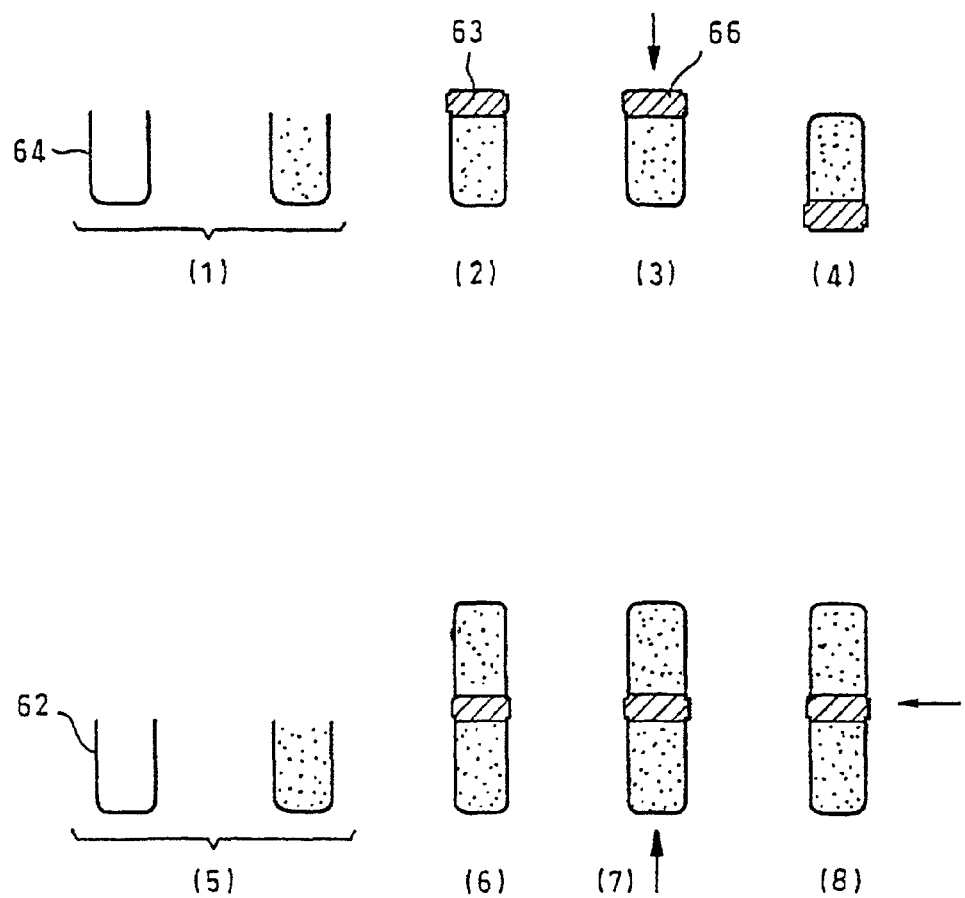

1

PHARMACEUTICAL FORMULATION

FIELD OF THE INVENTION

This invention relates to the preparation of an injection molded single or multi-component dosage forms using pharmaceutically acceptable polymeric blends.

BACKGROUND OF THE INVENTION

Various types of pharmaceutical dosage forms are known for oral dosing. Pharmaceutical capsules are well known, generally being intended for oral dosing. Such capsules generally comprise an envelope wall of a pharmaceutically acceptable, e.g. orally ingestible, polymer material such as gelatin, although other materials for capsule walls, e.g. starch and cellulose based polymers are also known. Such capsules generally have soft walls made by making a film on a capsule former, which is then allowed to dry. Rigid walled capsules made by injection molding are also known, see for example U.S. Pat. No. 4,576,284; U.S. Pat. No. 4,591,475; U.S. Pat. No. 4,655,840; U.S. Pat. No. 4,738,724; U.S. Pat. No. 4,738,817 and U.S. Pat. No. 4,790,881 (all to Warner Lambert). These disclose specific constructions of capsules made of gelatin, starch and other polymers, and methods of making them by injection molding of hydrophilic polymer-water mixtures. U.S. Pat. No. 4,576,284 specifically discloses such capsules provided with a cap which closes the capsule, and which is formed in situ on the filled capsule by molding. U.S. Pat. No. 4,738,724 discloses a wide range of rigid capsule shapes and parts.

Multi-compartment capsules, including those of the type where each compartment has different drug release characteristics, or for example, contains a different drug substance or formulation are also known, for example in U.S. Pat. No. 4,738,724 (Warner-Lambert); U.S. Pat. No. 5,672,359 (University of Kentucky); U.S. Pat. No. 5,443,461 (Alza Corp.); WO 95/16438 (Cortecs Ltd.); WO 90/12567 (Helminthology Inst.); DE-A-3727894, and BE 900950 (Warner Lambert); FR 2524311, and NL 7610038 (Tapanhony N.V.); FR 1,454,013 (Pluripharm); U.S. Pat. No. 3,228,789 (Glassman); and U.S. Pat. No. 3,186,910 (Glassman) among others. U.S. Pat. No. 4,738,817 discloses a multicompartment capsule with a similar construction to those of U.S. Pat. No. 3,228,789 and U.S. Pat. No. 3,186,910, made of a water-plasticized gelatin. U.S. Pat. No. 4,738,817 ('817) Witter et al., U.S. Pat. No. 4,790,881 ('881), Witter et al., and EP 0 092 908, Wittwer, F., all discloses injection molded capsules prepared with gelatin and other excipients. Wittwer et al. '817 and '881 also prepare capsules with other hydrophilic polymers, such as hydroxypropylmethylcellulose phthalate (HPMCP), methylcellulose, microcrystalline cellulose, polyethylene glycol, cellulose acetate phthalate (CAP) and with polyvinylpyrrolidone. Both U.S. Pat. No. 4,790,881 and EP 0 091 908 propose other polymers having enteric properties suitable for use, including generally acrylates and methacrylates (Eudragits) although none are demonstrated and no specific details are provided.

Pharmaceutical dosage forms are also known which comprise a matrix of a solid polymer, in which a drug substance is dispersed, embedded or dissolved as a solid solution. Such matrixes may be formed by an injection molding process. This technology is discussed in Cuff G, and Raouf F, Pharmaceutical Technology, June (1998) pages 96-106. Some specific formulations for such dosage forms are disclosed in U.S. Pat. No. 4,678,516; U.S. Pat. No. 4,806,337; U.S. Pat. No. 4,764,378; U.S. Pat. No. 5,004,601; U.S. Pat. No. 5,135,752; U.S. Pat. No. 5,244,668; U.S. Pat. No. 5,139,790; U.S. Pat. No. 5,082,655; U.S. Pat. No. 5,552,159; U.S. Pat. No. 5,939,099; U.S. Pat. No. 5,741,519; U.S. Pat. No. 4,801,460; U.S. Pat. No. 6,063,821; WO 99/27909; CA 2,227,272; CA 2,188,185; CA 2,211,671; CA 2,311,308; CA 2,298,659; CA 2,264,287; CA 2,253,695; CA 2,253,700; and CA 2,257,547 among others.

U.S. Pat. No. 5,705,189, is directed to a group of co-polymers of methacrylic acid, methyl methacrylate and methyl acrylate, for use as thermoplastic agents in the production of drugs coatings, and capsules. No information is presented on the quality of the capsule formation with respect to warping or other distortions produced by the injection molding process. Nor is shear rate data presented for the viscosity/temperature figures of the emulsions presented therein.

It would also be desirable to prepare a pharmaceutical dosage form in which a pharmaceutically acceptable polymeric blend is extruded by hot melt, or injection molded into a suitable dosage form, which may be multicompartmental, such as a capsule. This pharmaceutical polymeric composition as the dosage form, may provide differing physio-chemical characteristics for each segment containing an active agent, such that a convenient dosage form can be optioned which may include a rapid dissolve, immediate, delayed, pulsatile, or modified release which can be produced by simply selecting the appropriate polymer(s) to be molded for each section.

SUMMARY OF THE INVENTION

The present invention provides pharmaceutical compositions, injection molded capsule shells, linkers, spacers, multicomponent injection molded capsule shells, linkers or spacers, multicomponent pharmaceutical dosage forms, and other aspects as defined in the claims and description of this application.

It is an object of this invention to provide an alternative and improved pharmaceutical dosage form which provides, inter alia, greater flexibility in the dosage form adapted to a patient's specific administration requirement, and ease of manufacture.

Another object of this invention is to provide a process of producing a multicomponent dosage form comprising a pharmaceutically acceptable polymeric blend by injection molding. These multi-component dosage forms are suitable for containing a pharmaceutically acceptable active agent, or agents, for release thereby.

The present invention is also directed to the novel formulation or composition of a pharmaceutically acceptable polymer and suitable excipients to be used for injection molding of the capsules or multi-component dosage forms.

Another embodiment of the present invention is directed to the solid dosage form comprising a capsule compartment bounded by a wall made of a pharmaceutically acceptable polymeric formulation/composition, and optionally containing a drug substance.

In accordance with the invention, a multi-component, injection molded capsule shell is provided for, having at least one shell, linker or spacer with a composition, preferably including Eudragit 4135F, and further, preferably having it's components welded together.

More particularly, a preferred embodiment of the invention is a multi-component pharmaceutical dosage form, comprising a plurality of sub-units, each sub-unit being either a drug substance-containing capsule compartment which is soluble or disintegrable in a patient's gastro-intestinal environment for release of the drug substance contained in the capsule compartment, or a solid matrix comprising a polymer and containing a drug substance, the polymer being soluble, dispersible or disintegrable in a patient's gastrointestinal environment for release of the drug substance contained in the solid matrix. At least prior to administration to a patient, the sub-units are welded together in an assembled dosage form.

If a solid matrix is used as one of the sub-units, it preferably comprises Eudragit 4135F present in an amount of about 20 to 90% w/w, and a dissolution-modifying excipient present in an amount of about 2.5 to about 30% w/w. The solid matrix also preferably comprises a lubricant present in an amount up to about 30% w/w, a plasticizer present in an amount up to about 10% w/w, and a processing agent present in an amount up to about 10% w/w.

In an alternative preferred embodiment, the pharmaceutical dosage form comprises a plurality of sub-units, each being a drug substance-containing capsule compartment. In this case, each compartment is physically separated from at least one adjacent compartment, preferably by a wall made of a pharmaceutically acceptable polymer material. In a preferred embodiment, the wall comprises Eudragit 4135F, present in an amount of about 50 to 90% w/w, and a dissolution-modifying excipient present in an amount of about 2.5 to 30% w/w. As in the case of the solid matrix, the wall preferably comprises a lubricant present in an amount up to about 30% w/w, a plasticizer present in an amount up to about 10% w/w, and a processing agent present in an amount up to about 10% w/w.

In the case in which at least one of the sub-units is a drug substance-containing capsule compartments its wall thickness is preferably in the range of about 0.3-0.8 mm.

The multi-component dosage form of the invention affords a high degree of versatility in that it can be composed of various combinations of different dosage forms having different release characteristics. For example at least one of the sub-units can be a substantially immediate release sub-unit, a sustained release sub-unit, or a pulsed release sub-unit.

Another advantage afforded by a preferred embodiment of the invention is interchangeability of components. Thus, a set of multi-component dosage forms may be provided, each comprising a plurality of sub-units. Each sub-unit may be either a drug substance-containing capsule compartment which is soluble or disintegrable in a patient's gastro-intestinal environment for release of the drug substance contained in the capsule compartment, or a solid matrix comprising a polymer and containing a drug substance, the polymer being soluble, dispersible or disintegrable in a patient's gastro-intestinal environment for release of the drug substance contained in the solid matrix. At least one of the dosage forms of the set comprises at least one such drug substance-containing capsule compartment and at least one other dosage form of the set comprises at least one such solid matrix, and the drug substance-containing capsule compartment the one dosage form is interchangeable with the solid matrix of the other dosage form. Thus, in the manufacturing process, selected components can be welded together in various combinations to provide an assembled dosage form for administration to a patient.

Another important advantage of the invention resides in the process by which the constituents of the capsule compartments are prepared for injection molding. Especially in the case of an injection-molded, thin-walled capsule compartment composed of a poly(meth)acrylate copolymer and excipients such as dissolution modifiers, lubricants, release agents and strengtheners, it is important that the material forming the capsule compartment be homogeneous. It is also important that the material be processed at a sufficiently low temperature to avoid degradation of the polymer and the excipients. In accordance with the invention, a high degree of homogeneity is achieved by introducing the copolymer and an excipient composition simultaneously, and at substantially the same location, into an elongated hot melt extruder. The polymer and the excipient composition are mixed in the hot melt extruder to form the homogeneous composition therein and the composition is ejected from the hot melt extruder in the form of a strand though a die at a location remote from the location at which the polymer and excipient composition are introduced. The strand is cut into pellets, and the pellets are then introduced into an injection molder which forms thin-walled capsule compartments. Pharmaceutical dosage forms are assembled using the capsule compartments as components.

In order to avoid degradation of the polymer and the excipient composition, the hot melt extruder should be maintained at a temperature not exceeding approximately 135° C., and preferably at a temperature not exceeding approximately 125° C. In a preferred embodiment, the temperature gradually increases along the length of the hot melt extruder, from the location at which the polymer and excipient composition are introduced, to the die, the maximum temperature not exceeding approximately 135° C.

The process injection molding of the thin-walled capsule compartments is preferably carried out while maintaining the injection molder barrel at a temperature in the range of about 120° C. to 140° C., and maintaining the injection molder nozzle at a temperature in the range of about 140° C. to 190° C. Preferably the nozzle temperature is about 165 to 170° C.

A thin-walled capsule compartment is advantageous especially where quick dissolution of the capsule is desired. However, the wall thickness of conventional capsule shells is generally uniform, and in the range of about 0.3 mm to 0.5 mm., in order to achieve adequate strength, allowing the capsule shells to be formed and handled without breakage or distortion.

In accordance with another aspect of the invention, a preferred, molded pharmaceutical capsule component is defined by a generally frusto-conical side wall, a dome-shaped end wall situated at, and connected to, one end of the side wall, and an annular rim portion disposed at an opposite end of the side wall, the side wall, the dome, and the annular rim portion together forming a hollow receptacle having an interior and an exterior, and an open end opposite the dome-shaped end wall. The side wall is composed of a plurality of panels, each having a thickness in the range of about 0.2 to 0.3 mm, and reinforcing ribs integrally molded with the panels, each panel being situated between a pair of the reinforcing ribs.

The reinforcing ribs are preferably formed on the exterior of the hollow receptacle, and extend over at least a part of the dome-shaped end wall toward a centrally located peak, and gradually decrease in thickness as they approach the peak. In a preferred embodiment, the annular rim portion extends radially outwardly beyond the panels and comprises a tapered frusto-conical exterior surface. The reinforcing ribs have ends which meet, and are connected to, the tapered frusto-conical surface of the annular rim portion. The thickness of the ribs, at their ends which meet the rim portion, is preferably substantially equal to the distance through which the annular rim portion extends outwardly beyond the panels, so that the ribs merge smoothly with the rim portion.

Other objects and advantages of the invention will be apparent from the following description.

BRIEF DESCRIPTION OF THE DRAWINGS

FIG. 10 is a longitudinal sectional view of another dosage form of the invention assembled together.

FIG. 12 is an assembly sequence of a dosage form of FIG. 11A.

DETAILED DESCRIPTION OF THE INVENTION

Figure 1:
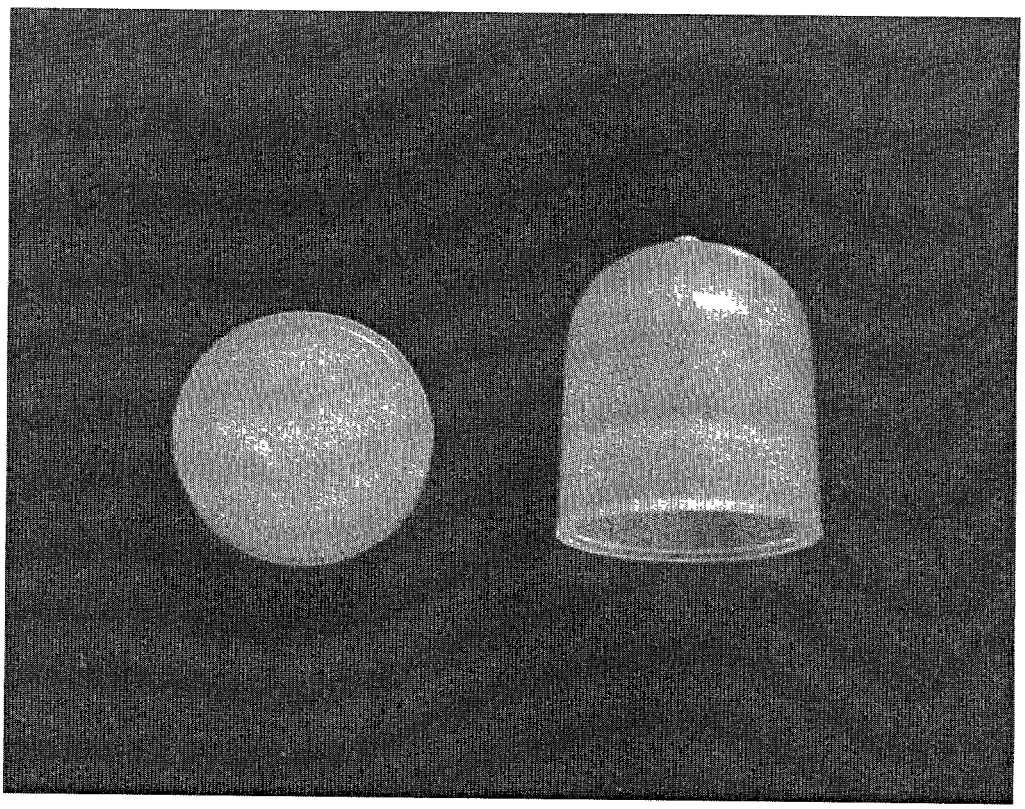
FIG. 1—shows injection-molded components comprising Eudragit 4135F 75%, Explotab 20%, stearyl alcohol 5%.

The present invention is directed to novel compositions of a pharmaceutically acceptable polymer and excipients, which polymeric composition may be injection molded into one or more components which can be utilized together, such as in a stacked or multi-component dosage form. It is recognized that the polymeric blends may be injection molded into a single component that may also contain the active agent for oral administration.

The pharmaceutically acceptable polymeric blends as a final dosage form may be designed to provide rapid dissolution, immediate, delayed, or modified dissolution, such as sustained and/or pulsatile release characteristics.

It is one object of the present invention to provide a final dosage form containing a pharmaceutically acceptable drug in a pharmaceutically acceptable polymeric blended multi-component dosage form.

The parts of the dosage form of this invention, e.g. a capsule compartment wall, a solid sub-unit, or a closure or linker, may comprise a pharmaceutically acceptable polymeric blend (and adhesive material if adhesive welds are formed) which is generally regarded as safe, e.g. for oral ingestion and is capable of being formed into the required shape of a capsule compartment wall, a solid sub-unit, or a closure or linker as described above. A preferred method of forming the polymer material into the desired shape is injection molding, which may be a hot or cold runner injection molding process. Suitable injection molding machines for such a process are known.

The pharmaceutical dosage form may comprises a plurality of capsule compartments each bounded and physically separated from at least one adjacent compartment by a wall made of a pharmaceutically acceptable polymer material, adjacent compartments being connected together in the assembled dosage form, and being retained together by the connection at least prior to administration to a patient, one or more of the compartments containing a drug substance. Suitably in the assembled dosage form of this first embodiment there are at least two, for example three, such capsule compartments. Three or more such compartments may be linearly disposed in the assembled dosage form, e.g. in an arrangement comprising two end compartments at opposite ends of the line, and one or more intermediate compartments. Suitably there may be two such capsule compartments. Suitably one of such two capsule compartments may be made of a material which is a sustained release component, i.e. so that the capsule compartment wall dissolves, bursts or is otherwise breached to release its contents after a time delay, e.g. when the compartment has reached the intestine. Suitably the other of such two capsule compartments may be made of a material which is an immediate release component, i.e. so that the capsule compartment wall dissolves, bursts or is otherwise breached to release its contents immediately or effectively immediately, e.g. when the compartment is in the mouth or stomach.

One or more, e.g. all, of the capsule compartments may for example be substantially cylindrical, which term includes shapes which have a circular, oval or oblate circular cross section across the longitudinal axis, and shapes which have parallel or tapering e.g. with side walls which taper conically over at least part of their extent. Such substantially cylindrical capsule compartments may be provided with connectible parts at one or both of their longitudinally disposed ends so that the assembled dosage form may also be overall of a substantially cylindrical shape.

A preferred form of the multi-component dosage form of this invention comprises two capsule compartments.

The invention also provides individual sub-units, e.g. individual capsule compartments or solid sub-units adapted for use in the assembled dosage form.

In the assembled dosage form, the adjacent capsule compartments may be connected together by means of a weld at the area where two adjacent parts of the dosage form, e.g. sub-units, are in contact, e.g. a thermal weld, an ultrasonic or inductive weld, or an adhesive weld (e.g. curable adhesives such as UV curable adhesive). A thermal weld may for example be achieved by bringing sub-units into adjacent contact and applying localised heating for example produced by directing a laser beam or a fine jet of hot gas e.g. nitrogen at the area where two adjacent sub-units are in contact. In thermal, inductive and ultrasonic welding normally localised fusion together of the materials of adjacent parts of the dosage form which are in contact occurs, and on subsequent solidification of the materials a bond is formed between the adjacent parts. An adhesive weld may be achieved by applying an adhesive (e.g. curable adhesives such as UV curable adhesive) to parts of the dosage form which when the dosage form is assembled are in contact, and then causing or allowing the adhesive to set.

The multi-component dosage form of the present invention is particularly suited to fabrication using ultrasonic welding. Ultrasonic welding is a known technique involving the use of high frequency sound energy to soften or melt a thermoplastic material at the site where a joint with the material is required. A general description of ultrasonic welding is for example to be found in the publication "Ultrasonic Welding of Thermoplastics" (TWI Ltd., Abington, Cambridgeshire GB, (1997)). Parts to be joined are held together under pressure and then subjected to ultrasonic vibrations usually at a frequency of 20-40 kHz. The actual mechanism responsible for the generation of heat at the joint site is not well understood. An ultrasonic welding machine comprises five main components, being a power supply, a control system, a welding head, fixturing to hold the parts to be welded, and a system to apply the required pressure. The power supply converts electricity into high frequency electric power which drives a transducer, e.g. a piezoelectric transducer, which converts electrical energy, e.g. from the mains supply, into mechanical, i.e. ultrasonic, energy. Between the transducer and the parts to be welded is located a booster and horn system, being a usually metallic component which serves to amplify the ultrasonic waves (the booster horn), transmit the clamping pressure, and deliver the sound energy to the part to be welded (the sonotrode or welding horn). For successful ultrasonic welding careful design of the parts to be welded and set up of the welding equipment is important.

Preferably, additionally or alternatively adjacent sub-units may be provided with respectively interconnectible first and second connectible parts such that the first connectible part on one sub-unit may connect with the second connectible part on an adjacent part of the dosage form, e.g. an adjacent sub-unit in a suitable configuration, e.g. in the above-mentioned linear configuration. This interconnection may contribute to the strength of bond achieved by the weld, or additionally or alternatively may help to hold adjacent parts of the dosage form together prior to and in readiness for the weld to be formed and contributes to the retention of the adjacent sub-units together, e.g. via a retaining friction, snap, screw or other kind of fit between the connectible parts. The connectible parts may be such as to facilitate the assembly together of the sub-units in preferred configurations, e.g. the connectible part(s) on one or more one sub-unit may be such as to only connect with a corresponding connectible part on other selected sub-units but not with non-corresponding connectible parts on other sub-units. Alternatively the connectible parts on the sub-units may be common and interchangeable so that the sub-units may be connected together in a wide range of combinations. This means inter alia that otherwise different capsule compartments or solid sub-units may have mutually connectible parts so that the different capsule compartments or solid sub-units may be connected together in different combinations of solid sub-units or solid sub-units and capsule compartments.

For example in one embodiment the respective first and second connectible parts may be respectively interlocking parts. For example, the first or second part may be a socket part, and the corresponding second or first connectible part may be a corresponding plug part which fits into the socket with a retaining friction, snap, screw or other kind of interlocking fit. If for example these plug and socket parts are common, then any plug part on any solid sub-unit or capsule compartment may interconnect with any socket part on another solid sub-unit or capsule compartment.

In a friction fit for example the plug part may be slightly larger than the socket such that force needs to be applied against the natural resilience and contact friction of the plug and socket parts to cause the plug part to enter the socket, and similar force needs to be applied to separate them. In a snap fit for example the plug and socket parts may be respectively provided with a concavity and a corresponding convexity, such as a ridge and groove, which lock together as the parts are forced together against the natural resilience of the parts. Such a ridge and groove may for example comprise a co-operating circumferential or part circumferential bead and groove, for example located about the circumference of a connectible plug and socket part.

The above-described first and second connectible parts facilitate assembly of sub-units together in various ways.

For example in a dosage form of the invention comprising a linear disposition of three or more e.g. four, sub-units, an intermediate sub-unit may be provided with one or more connectible parts for example one at each end, which may connect with one or more connectible part on an adjacent intermediate sub-unit. An end sub-unit may be provided with one or more connectible part which may connect with a connectible part on an adjacent intermediate sub-unit and/or with one or more connectible part on another end sub-unit. By means of this two end sub-units may connect together in a dosage form comprising two sub-units, or two end sub-units may be connected to one or more intermediate sub-units. By using common first and second connectible parts on the sub-units the various end and intermediate sub-units may be made such that they may be connected together in various combinations of assembled dosage forms.

One or more sub-unit which is a capsule compartments may for example be substantially tub-shaped, i.e. having a base closed by a base wall, and side walls extending from the base wall (herein referred to as an "upward" direction), and an upper open mouth. With such a construction capsule compartments may connect together by the base of a first compartment fitting into the open mouth of an adjacent second capsule compartment, so as to close the mouth of the adjacent capsule compartment, and such that the base wall of the first compartment physically separates the compartments. In such a construction the base of the first compartment comprises a plug connectible part, and the mouth opening of the second compartment comprises a socket connectible part.

For example the dosage form may include one or more linker unit positioned between adjacent pairs of capsule compartments, preferably with at least one weld in the dosage form may be between a capsule compartment and such a linker unit. Such a linker unit may for example have connectible parts which are connectible to the above-mentioned first and/or second connectible parts on the adjacent capsule compartments. Suitably to facilitate a linear assembly of capsule compartments in the dosage form a linker unit may have its connectible parts in opposite linear facing directions. Suitably such a linker unit may comprise a closure for the mouth opening of a capsule compartment, e.g. connecting with the capsule compartment in the manner of a plug or a cap for its mouth opening, and having a connectible part enabling connection to an adjacent sub-unit, e.g. another capsule compartment. If a capsule compartment is made of a sustained release component, then preferably such a linker/closure is also made of a sustained release component, so that the entire capsule compartment envelope of compartment and closure is a sustained release envelope.

In a specific form the linker may have one or two connectible parts which connect with the mouth opening of a capsule compartment. For example such a linker may have two connectible parts which are opposite facing plug parts and which can connect in a plug and socket manner with the mouth opening of two oppositely-facing capsule compartments to thereby form a capsule-linker-capsule assembly. Suitably welds, e.g. ultrasonic welds, may be formed between both of the capsule compartments and the linker between them in such a dosage form.

For example a linker may comprise a closure for the mouth opening of a capsule compartment, and this linker may have one or more first and/or second connectible parts such that the first or second part on the closure may connect with respectively the second or first part on an adjacent capsule compartments in a suitable configuration.

For example in one form such a linker/closure may be provide with two oppositely-facing plug connectible parts which can connect with the mouth openings of opposite-facing capsule compartments. Such a closure can thereby act as a linker between two capsule compartments with their mouth openings oppositely facing, in a capsule compartment-linker-capsule compartment linear arrangement. For example this arrangement may be an end compartment-linker-end compartment arrangement.

Other ways in which such a linker may be used in a dosage form of the invention will be apparent. For example an intermediate capsule compartment may be in the form of a generally cylindrical shape with two oppositely facing open ends, and two linkers may connect via respectively one each of their connectible parts with an open end of the cylinder, leaving the other connectible part available for connection to respectively another sub-unit.

Preferably at least one, or both, of the connectible parts of the linker is a plug part which fits in a plug-and-socket manner into the open end of a capsule compartment. Therefore such a plug part is typically a cylindrical shape, corresponding closely to the internal shape of the open end of a capsule compartment adjacent to the open end.

Preferably the linker is in the form of a solid wall part with oppositely facing plug connectible parts, oppositely facing end surfaces of the plug parts extending generally transverse to the longitudinal direction of the linker. Preferably each plug part is a snug friction fit into the open end of a capsule compartment. Preferably each plug part is provided with an abutment surface to define and limit the extent to which each plug part can extend into the open end of a capsule compartment by abutting against the rim of the open end of a capsule compartment when the plug part extends to a suitable extent into the capsule mouth.

In a preferred construction, the linker comprises a generally cylindrical solid body, its opposite facing ends being plug parts, with two oppositely facing abutment surfaces each being a surface of a ledge formed around the circumference of the cylindrical body and generally planar in a plane perpendicular to the length direction. Such a ledge may typically be ring shaped with its plane perpendicular to the longitudinal direction of the capsule. With such a linker the assembled dosage form may comprise two capsule compartments each in the shape of a cylinder having one open end and one closed end (e.g. the above-described tub or bucket shapes), with their open ends in an opposite facing relationship, with a linker between them with each of the opposite facing plug parts of the linker fitting in a plug-and-socket manner into the open end of a capsule compartment, with an ultrasonic weld formed between a plug part and/or an abutment surface of the linker and the compartment wall in the vicinity of the open end, e.g. the rim of the open end.

A preferred construction of multicompartment capsule assembly comprises a capsule compartment made of a sustained release component, capsule compartment made of an immediate release component, and a linker between them made of a sustained release component. In such a construction the immediate release compartment may breach and release its content, leaving the envelope of compartment and closure as a sustained release envelope to release its contents in e.g. the intestine.

In the process of injection molding a fluid polymer is injected under pressure into a precisely made die cavity in a mold block. Injection molding processes can enable the sub-units to be made with the precision necessary to achieve connection by tight friction-fit or snap-fit interlocking and to maintain suitable contact between adjacent parts to facilitate a weld. Suitable techniques of injection molding are known from for example the art of manufacture of small plastic components e.g. small parts of LEGO® toys. Processes such as those described in Cuff. G and Raouf. F, supra, may be used to manufacture such solid sub-units and capsule compartments via injection molding.

Consequently the invention also provides for a molding process, for example an injection molding or powder compression process, wherein sub-units, including the solid sub-units and capsule compartments of the dosage form are made in respective mold cavities of the pharmaceutically acceptable polymeric blends.

Details of the multi-component dosage forms referred to above will now be described with reference to FIGS. 6-11.

Figure 6:
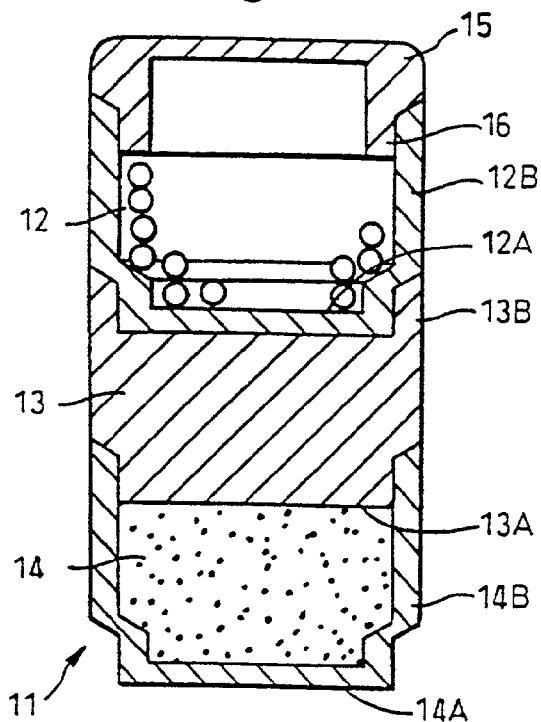
FIG. 6 is a longitudinal sectional view of a dosage form of the invention assembled together.

Referring to FIG. 6, a dosage form 11 is shown comprising three sub-units 12, 13, 14 linearly disposed in the assembled dosage form, in an arrangement comprising two end compartments, 12 and 14, at opposite ends of the line, and one intermediate solid sub-unit 13. The compartments 12 and 14 and the solid sub-unit 13 are substantially cylindrical. The compartments 12 and 14 are substantially tub shaped; i.e. each has a base closed by a base wall 12A, 14A, and each has side walls 12B, 14B extending upward from the base wall 12A, 14A, and an upper mouth. Each of the compartments 12 and 14 is made of polyvinyl alcohol polymer by injection molding.

The solid sub-unit 13 is also substantially cylindrical, and has its base end 13A formed into a plug shape capable of engaging with and thereby closing the mouth of either compartment 12 or 14. As shown in FIG. 6, the base end 13A of solid sub-unit 13 fits into and is in engagement with the mouth opening of compartment 14. The upper end of solid sub-unit 13 has its upper end 13B formed into a socket connector capable of engagement with the shape of the base 12A or 14A of capsule compartment 12 or 14. As shown in FIG. 6, the socket at the upper end 13B of the solid sub-unit 13 is in engagement with the base of compartment 12.

The compartments 12, 14 and solid sub-unit 13 connect together by fitting the base 12A of compartment 12 into the upper socket 13B of adjacent solid sub-unit 13, and fitting the base 12A of the solid sub-unit 13 into the mouth of adjacent compartment 14 so as to close its mouth. In this assembly of sub-units 12, 13, 14, the base part of an upper sub-unit 12, 13 comprises a plug part and the mouth opening or upper socket of a lower sub-unit respectively 13, 14 comprises a socket.

Compartment 14 is an end compartment, and has its mouth opening closed by the base end 13A of solid sub-unit 13. The other upper end compartment 12 is closed by a closure 15, having a plug part 16 which is dimensioned to fit into the mouth opening of the compartment 12.

The plug part 16, and the base parts 12A and 13A, fit respectively into the mouth opening of compartment 12, the socket of solid sub-unit 13, and the mouth opening of compartment 14. Thermal welds are formed between the plug part 16, base parts 12A and 13A, and the respective mouth openings and upper socket of the compartments 12, 14 and the solid sub-unit 13 at the regions where these parts are in contact. Each of the base parts 12A, 13A, and the plug part 16, and the corresponding respective mouth openings and upper socket of the compartments 12, 13 and 14 may additionally or alternatively be provided with features (not shown) such as a convex circumferential bead and a corresponding circumferential groove into which the bead may fit, such that the base part 12A, 13A, the mouth openings of the compartments 12 and 14, the upper socket 13B and the plug part 16 and mouth opening of compartment 12 may connect together by snap fit interlocking engagement, overcoming the natural resilience of the polymer material of the base part and mouth opening.

The thermal welds may be formed between the plug part 16, the base parts 12A and 13A, and the mouth openings and upper socket of the compartments 12, 14 and the solid sub-unit 13, by directing a laser beam to the region where these parts are in contact.

The base parts 12A, 13A, 14A of the compartments 12, 13, 14, the mouth openings of the compartments 12 and 14, the upper socket 3B and the plug part 16 are preferably all of common dimensions so that the compartments 12 and 14 and the solid sub-unit may be fitted together in other linear combinations, and so that the plug 15 may be used to close the mouth opening of the other compartments 14.

Similarly, two or more than the three sub-units 12, 13 or 14, may be connected together in a manner analogous to that shown in FIG. 1.

Figure 7:
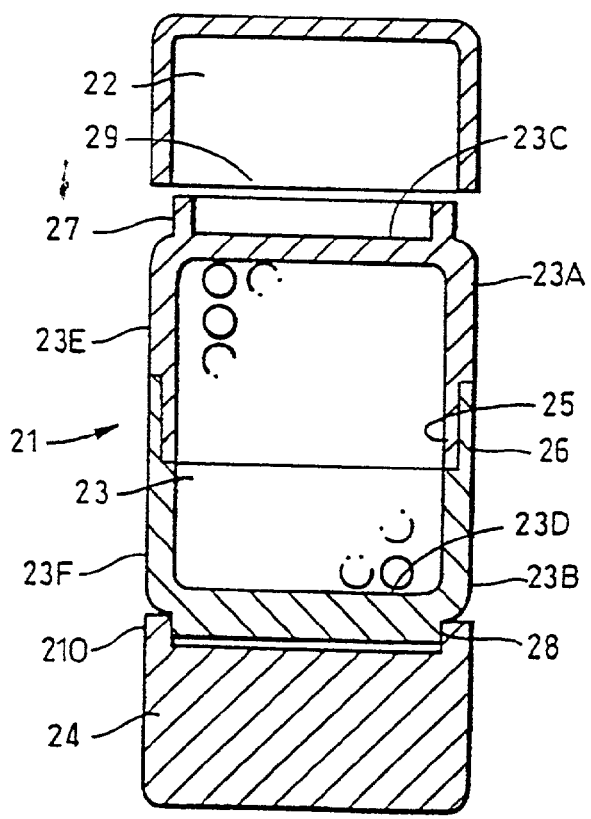
FIG. 7 is a longitudinal sectional view of another dosage form of the invention, partially assembled.

FIG. 7 shows another dosage form assembly 21. This assembly 21 also comprises three sub-units 22, 23. 24 in a linear assembly consisting of an end compartment 22, an intermediate compartment 23 and a solid end sub-unit 24. The intermediate compartment 23 is composed of part compartment shells 23A and 23B, the part shells 23A, 23B comprising respectively a closed end 23C and 23D and side walls 23E and 23F with a mouth opening opposite each closed end 23C and 23D. The mouth openings of the two part shells 23A and 23B are each provided respectively with connectible plug and socket parts 25 and 26. By engagement of their respective plug and socket parts 25 and 26, these part shells 23A, 23B are connected together to form the capsule compartment 23. The closed ends 23C, 23D are provided with external connectible parts 27, 28.

The end compartment 22 is in the form of a tub-shaped compartment and has a mouth opening 29, which comprises a socket part that corresponds in shape with connectible part 27 on the intermediate compartment 23 to connect the assembly 21 together.

Figure 2:
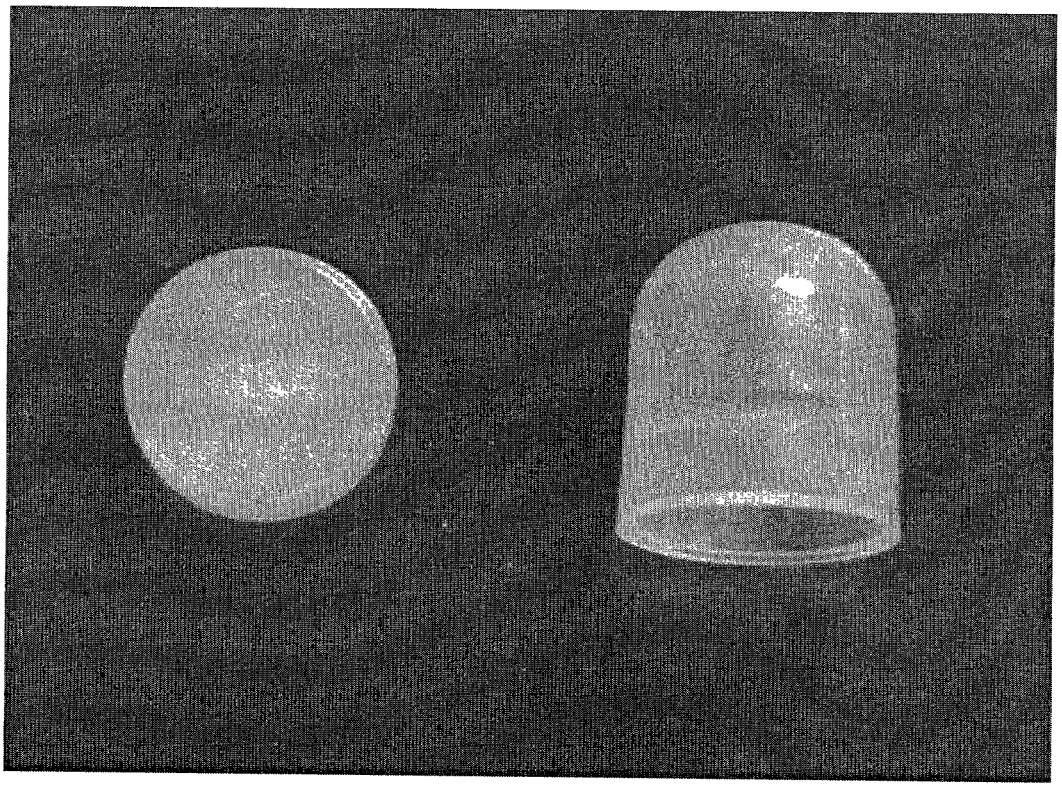
FIG. 2—shows injection-molded components comprising Eudragit 4135F 73%, Pharmacoat 603 10%, Lactose 5%, stearyl alcohol 12%.
Figure 3:
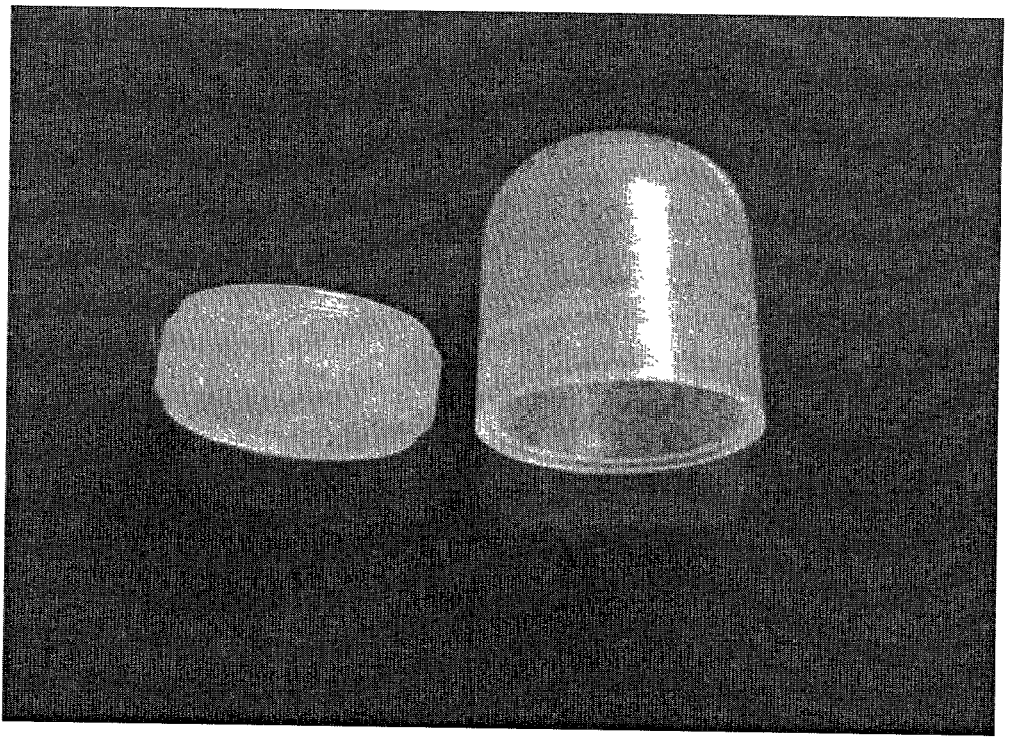
FIG. 3—demonstrates a dissolution profile of the polymeric composition of Eudragit 4135F 75%, Explotab 20%, stearyl alcohol 5%, the shells welded to Eudragit 4135F linkers, the dissolution media used was pH 7.5 Simulated Intestinal Fluid (SIF)

The end solid sub-unit 24 is formed as a substantially cylindrical body, having a connectible part 210 in the form of a socket engageable with either of the connectible parts 27 or 28 on intermediate capsule compartment 23. As shown in FIG. 2 the connectible part 210 on solid sub-unit 24 is connected to the part 28 on capsule compartment 23.

As with the dosage form of FIG. 6, a thermal weld is formed between the parts 25,26, 27, 29, 28 and 210 at the region where these parts are in contact. Each of these parts 25, 26, 27, 29, 28 and 210 may additionally or alternatively be provided with features (not shown) such as respectively a convex circumferential bead and a circumferential groove into which the bead may fit, such that these interlocking parts may connect together by a snap fit engagement.

Figure 8A:
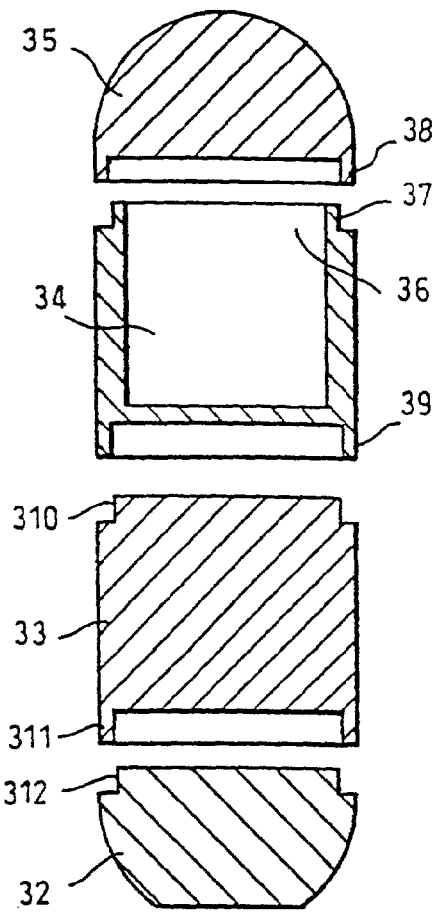
FIG. 8A is a longitudinal, exploded, sectional view of another dosage form of the invention.

FIG. 8A shows another dosage form assembly 31. This assembly 31 comprises four sub-units 32, 33, 34, 35 in a linear assembly consisting of an end solid sub-unit 32, an intermediate solid sub-unit 33, a tub-shaped, intermediate capsule compartment 34 and an end solid sub-unit 35. The intermediate capsule compartment sub-unit 34 has a mouth opening 36, and the immediately adjacent rim 37 of this mouth opening 36 is formed as a plug connectible part. The end solid sub-unit 35 is substantially hemispherical and is formed as a closure cap for the tub-shaped intermediate capsule compartment 34, being formed at its lower end as a socket connectible part 38 which fits in a sealing engagement with the part 37. The closed lower end of compartment 34 is externally provided with a socket connectible part 39.

The intermediate solid sub-unit 33 has its upper end formed as a plug connectible part 310 engageable with the part 39 of the compartment 34, and a lower end formed as a socket connectible part 311.

The end solid sub-unit 32 has a flat bottom and a truncated spherical exterior, with a plug connectible part 312 that corresponds in shape with connectible part 311 on the intermediate compartment 33. Each of these parts 37, 38,39,310, 311, 312 may additionally or alternatively be provided with features (not shown) such as respectively a convex circumferential bead and a circumferential groove into which the bead may fit, such that these interlocking parts may connect together by a snap fit engagement.

Figure 8B:
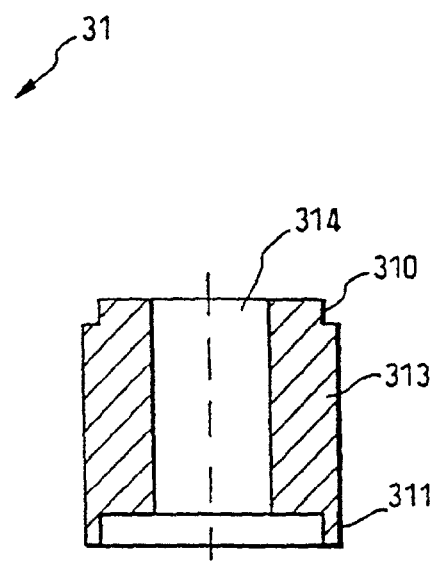
FIG. 8B is a longitudinal sectional view of an alternative sub-unit for use in the dosage form of FIG. 8A.

In FIG. 8B, an alternative construction of the intermediate solid sub-unit 33 is designated by reference number 313, parts common with the sub-unit 33 being numbered correspondingly. The sub-unit 313 has a cylindrical internal bore 314 so that the sub-unit 313 is of a generally hollow, cylindrical shape. The bore 314 may alternatively be of a longitudinally tapering, e.g. generally cylindrical, shape.

By connection of the various connectible parts 37, 38, 39, 310,311, and 312 the assembly 31 may be connected together along the axis shown.

Figure 9:
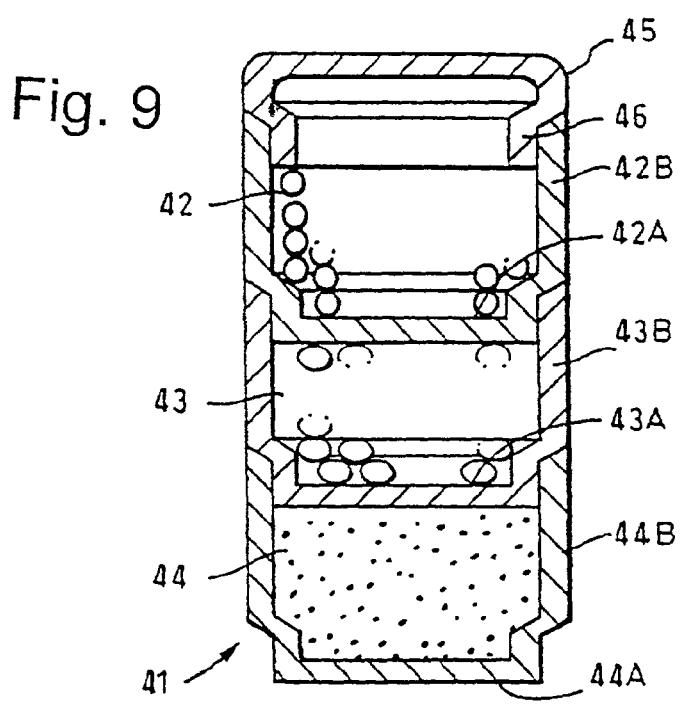
FIG. 9 is a longitudinal sectional view of a dosage form of the invention assembled together.

FIG. 9 shows a dosage form 41 comprising three capsule compartments 42, 43, 44, linearly disposed in the assembled dosage form, in an arrangement comprising two end compartments 42, 44 at opposite ends of the line, and one intermediate compartment 43. All of the compartments 42, 43, 44 are substantially cylindrical, and have an oval cross-section across the longitudinal axis. The compartments 42, 43, 44 are substantially tub-shaped, i.e. each having a base closed by a base wall 42A, 43A, 44A, a side wall 42B, 43B, 44B extending upward from the base wall 42A, 43A, 44A, and an upper mouth. Each of the compartments 42, 43 and 44 is made of a polymer such as Eudragit 4135F by injection molding.

The compartments connect together by the base 42A, 43A of a first compartment 42, 43 fitting into the open mouth of an adjacent second compartment respectively 43, 44 so as to close the mouth, and such that the base wall 42A, 43A of the first compartment 42, 43 physically separates the first and second compartments 42, 43 and 44. In this assembly of compartments 42, 43, 44 the base part of an upper compartment 42, 43 comprises a plug part and the mouth opening of a lower compartment respectively 43, 44 comprises a socket.

Compartment 44 is an end compartment and has its mouth opening closed by the base wall 43A of compartment 43. The other end compartment 42 is closed by a closure 45 having a plug part 46 which is dimensioned to fit into the mouth opening of the compartment 42.

The base parts 42A and 43A, and the plug part 46, fit into the respective mouth openings of the compartments 43, 44 and 42. A weld is formed between the base parts 42A and 43A, the plug part 46, and the respective mouth openings of the compartments 43, 44 and 42, for example by the application of local heating or an ultrasonic horn (not shown) to the region where these parts are in contact. Each of the base parts 42A, 43A, and the plug part 46, and the corresponding mouth openings of the compartments 43, 44 and 42 may additionally or alternatively be provided with features (not shown) such as a convex circumferential bead and a corresponding circumferential groove into which the bead may fit, such that the base part 42A, 43A and mouth openings of the compartments 43 and 44, and the plug part 46 and mouth opening of compartment 42 may connect together by a snap fit interlocking engagement overcoming the natural resilience of the polymer material of the base part and mouth opening.

The base parts 42A, 43A, 44A of the compartments and the mouth openings of the compartments 42, 43, 44, and the plug part 46 are all of common dimensions so that the compartments 42, 43 and 44 may be fitted together in other linear combinations, and so that the plug 45 may be used to close the mouth opening of any of the other compartments 42, 43 or 44.

Figure 4:
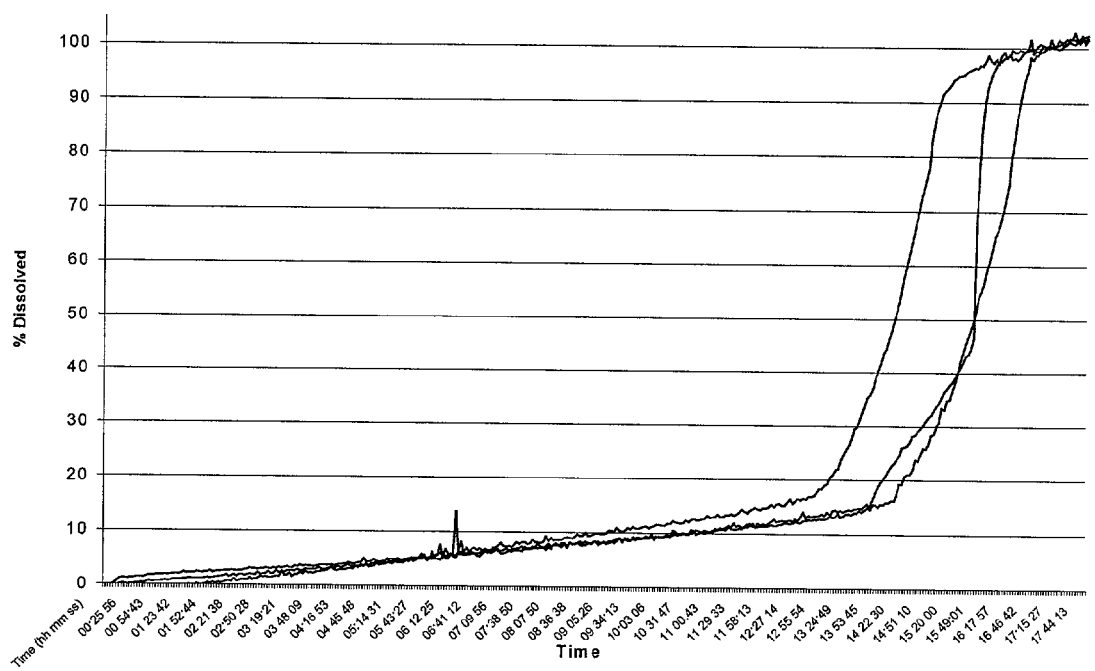
FIG. 4—demonstrates a dissolution profile of the polymeric composition of Eudragit 4135F 73%, Pharmacoat 603 10%, Lactose 5%, stearyl alcohol 12%, with the shells welded to 4135F12% stearyl alcohol linkers, the dissolution media used was pH 7.5, Simulated Intestinal Fluid.
Figure 5:
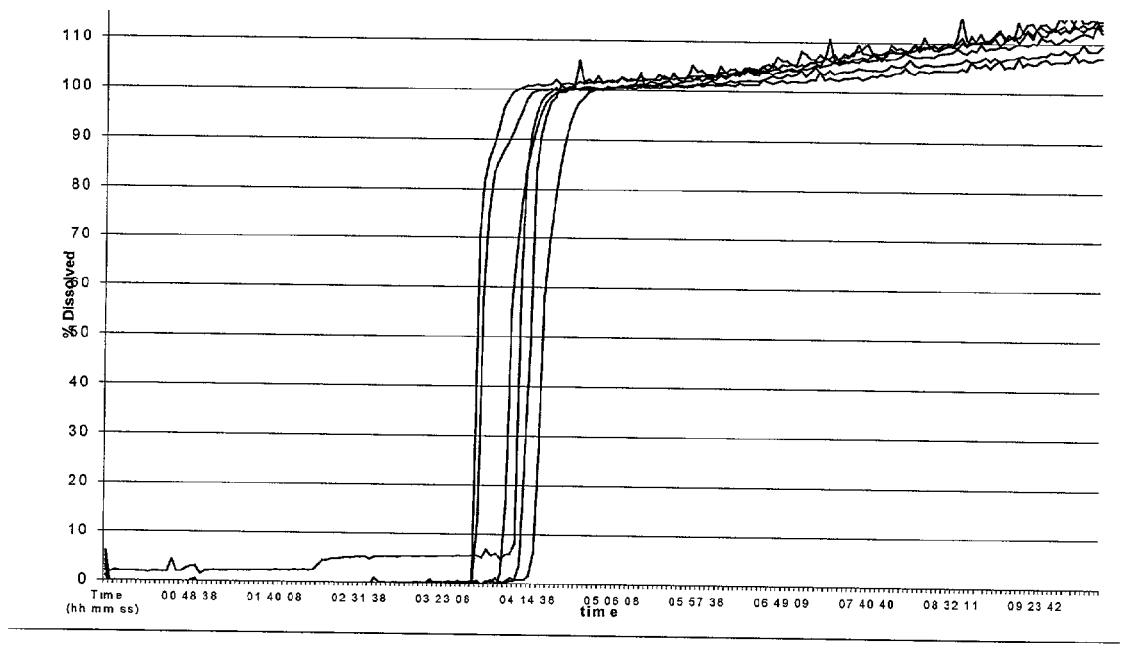
FIG. 5—demonstrates a dissolution profile of the polymeric composition of Eudragit E100 75%, PolyOx N-80 WSR 20%, stearyl alcohol 5%, welded to Eudragit 4135F linkers, the dissolution media used was pH 1.2 Simulated Gastric Fluid.

Similarly, two or more than the three compartments 42, 43 or 44, may be connected together in a manner analogous to that shown in FIG. 4.

FIG. 10 shows another dosage form assembly 51. This assembly 51 also comprises three compartments 52, 53, 54 in a linear assembly of two end compartments 52, 54 and an intermediate compartment 53. The intermediate compartment 53 is composed of two shells parts 53A and 53B, the shell part 53A comprising a closed end 53C and side walls 53E, and the shell part 53B comprising a closed end 53D and a side wall 53F. Each shell part has a mouth opening opposite its closed end. The mouth openings of the two shells part 53A and 53B are provided respectively with a plug connectible part 55 and a socket connectible part 56. The respective plug and socket parts 55 and 56 of these shell parts connect together to form the capsule compartment 53. Both of the closed ends 53C, 53D are externally provided with connectible plug parts 57, 58.

Each end compartment 52, 54 is in the form of a tub-shaped compartment and has a mouth opening, e.g. opening 59 of compartment 52, which comprises a socket part that corresponds in shape with the connectible plug parts 57, 58 on the intermediate compartment 53 to connect the assembly 51 together.

As with the dosage form of FIG. 9, a weld is formed between the parts 55, 56, 57, 58 and the respective mouth openings of the compartments 52, 54, by the application of local heating or an ultrasonic horn (not shown) to the region where these parts are in contact. Each of these parts 55, 56, 57, 58 and the respective mouth openings of the compartments 52, 54 may additionally or alternatively be provided with features (not shown) such as respectively a convex circumferential bead and a circumferential groove into which the bead may fit, such that these interlocking parts may connect together by a snap fit engagement.

Each of the compartments 42, 43, 44, 52, 54 in FIGS. 9 and 10 may be made of the same or different polymer and may have the same or different drug release characteristics. The intermediate compartments respectively of FIGS. 6 and 7 are more suitable for a modified release compartment, as dissolution or disruption of the end compartments can occur without disturbance of the intermediate compartments, and before dissolution or disruption of the intermediate compartments.

The compartments 42, 43, 44, 53, 54 and 55 in FIGS. 9 and 10 may contain the same or different drug substances and/or formulations. The drug substance or formulation may be, for example, in the form of powder, granulates, or other solid forms. Alternatively the compartments may contain liquid, gel or similar formulations (not shown).

Figure 11A:
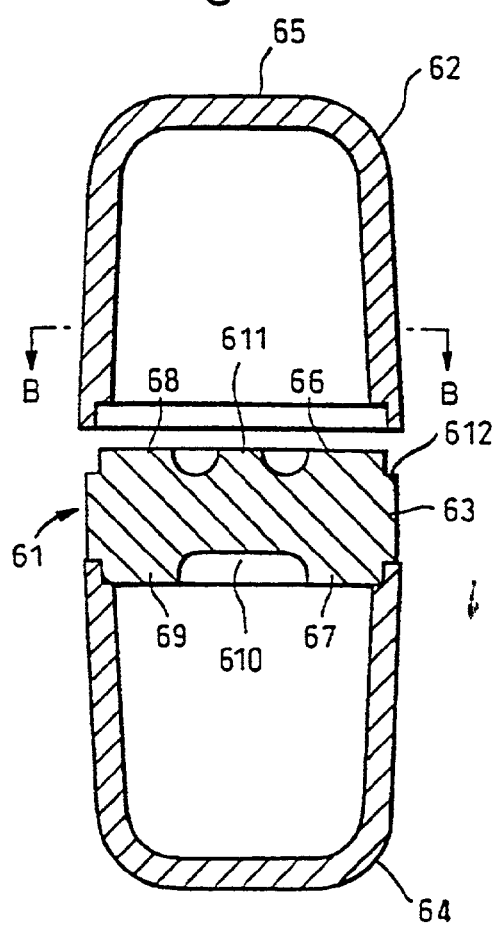
FIG. 11A is longitudinal sectional view of still another dosage form of the invention in partially assembled condition.
Figure 11B:
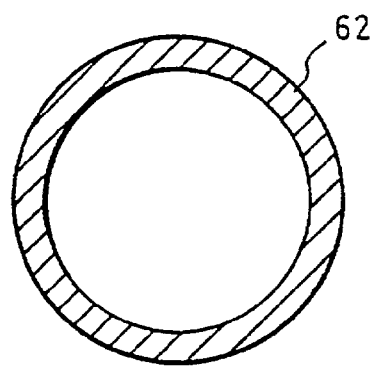
FIG. 11B is a cross section taken on plane B-B of FIG. 11A.
Figure 11C:
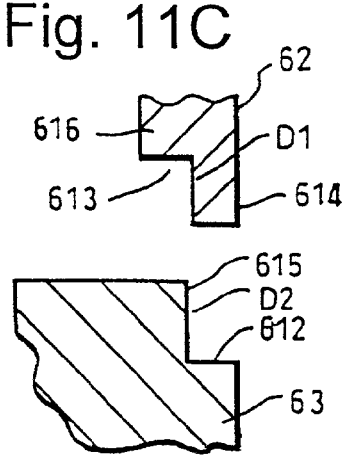
FIG. 11C is an enlarged, exploded view of a portion of the dosage form of FIG. 11A.

FIGS. 11A, 11B and 11C show another dosage form assembly 61. As shown in longitudinal section in FIG. 11A and in cross section in FIG. 11B, this dosage form is an assembly composed of an end capsule compartment 62, a linker 63, and another end capsule compartment 64 in a linear arrangement. Each end compartment 62, 64 has one open end and one closed end, and is generally in the shape of a cylinder, the compartments shown in FIG. 11A, having a slight conical taper, the cross section being greatest at the open end. The closed end is in the form of an end wall having a rounded periphery, giving the compartment forming an open ended "bucket" or "tub" shape. The central part of the rounded end of each compartment (designated 65 in the case of compartment 62) is flattened over at least 5% of the end surface area to facilitate the application of ultrasonic energy during a welding operation. The wall of each capsule compartment 62, 64 is ca. 0.4±0.05 mm thick in the side walls of the compartment.

The linker 63 is provided in the form of a solid wall with oppositely facing surfaces 66, 67 extending generally transverse to the longitudinal direction of the linker. These oppositely facing surfaces are the end surfaces of oppositely facing plug connectible parts 68, 69 formed at each of the longitudinal ends of the linker. The linker 63 is a generally cylindrical body flattened in the direction of its length, with a diameter:length ratio ca. 3:1. In a specific embodiment, the diameter of the linker 63 is ca 7.5 mm, and its length is ca. 3.0 mm. The end surfaces 66, 67 are substantially planar over at least 50% of their extent to facilitate application of ultrasonic energy thereto in the welding operation. The surface 67 is a planar ring-shaped surface surrounding a central concavity 610. The surface 66 is similar, except that, within the central cavity there is the residue 611 of an injection molding runner. The planar surfaces 66, 67 extend continuously over a dimension of at least 2 mm, i.e. having a surface area of at least 4 $mm^2$. Each plug part 68,69 fits snugly with a friction fit into the open end of a capsule compartment 62, 64. Each plug part 68, 69 is provided with an abutment surface 612 constituted by a ledge formed around the circumference of the cylindrical body 63. The abutment surface 612 is ring shaped with its plane perpendicular to the longitudinal direction of the capsule. The abutment surface 612 defines and limits the extent to which each plug part 68, 69 can extend into the open end of a capsule compartment 62, 64 by abutting against the rim of the open end of a capsule compartment 62, 64. In the specific embodiment shown, the abutment surface 612 is ca 0.3 mm wide measuring across the length direction.

An ultrasonic weld is formed between each plug part 68, 69 and/or an abutment surface 612 of the linker 63 and the compartment wall 62, 64 in the vicinity of the open end, e.g. the rim of the open end. The lower compartment 64 is shown formed in this way, the upper compartment 62 being shown disassembled.

For forming an ultrasonic weld between adjacent contacting parts of the capsule compartments 62, 64 and the linker 63, these parts are profiled and dimensioned to facilitate an ultrasonic shear joint, as shown enlarged in FIG. 11C. The connectible plug 68 and socket 613 comprise interlocking tenon parts 614, 615, where the length of one tenon 614 (D1 ca. 0.2-0.3 mm) is less than the length (D2 ca. 0.5-0.6 mm) of the other tenon part 615, and under the ultrasonic welding operation the material of the capsule compartment 62 in the region 616 can collapse until the tenon parts engage longitudinally to form the ultrasonic weld between the capsule compartment 62 and the linker 63. The weld between the linker 63 and the compartment 64 has been formed in a similar manner.

The length D2 of the plug part, being ca. 0.55 mm, is ca. 20% of the overall length of the linker 63 between the end surfaces 66 and 67.

FIG. 12 shows a typical assembly procedure for a dosage form of FIG. 11A. The procedure comprises the following steps:

(1) A first capsule compartment 64 is positioned and supported in a suitable holding means with its mouth opening pointing upwards, and the capsule compartment 64 is filled with a suitable quantity of a drug substance.

(2) A first plug part 69 (see FIG. 11A) of a linker 63 is inserted into the open end of the first capsule compartment 64. In this manner, the linker 63 forms a closure for the mouth opening of the capsule compartment 64.

(3) A downwardly pointing ultrasonic horn (not shown) is applied to the surface 66 of the linker, i.e. to the surface on the end of the linker opposite the first plug part 69, and an ultrasonic weld between the linker 63 and the first capsule compartment 64 is formed.

(4) The formed assembly of first capsule compartment 64 and linker 63 is inverted so that the plug part 68 (see FIG. 11A) is pointing downwards.

(5) A second capsule compartment 62 is positioned and supported in a suitable holding means (not shown) with its mouth opening pointing upwards, in a manner analogous to step 1, and the second compartment 62 is filled with a suitable quantity of drug substance.

(6) The plug part 68 of the linker 63 is inserted into the open end of the second capsule compartment 62.

(7) An ultrasonic horn (not shown) is applied to the outer surface of the second compartment 62 from underneath. An ultrasonic weld is formed between the linker 63 and the second capsule compartment 62.

In an alternative welding mode shown as step (8), an ultrasonic horn (not shown) is applied laterally, as shown by the arrow, to the side of the region of contact between the capsule compartment 64 and the linker 63.

In other alternative modes, (not shown) thermal, laser or adhesive welds may be formed between the capsule compartments 62 and 64 and the linker 63.

Each of the compartments and sub-units in FIGS. 1 to 6 may be made of the same or different polymer and may have the same or different drug release characteristics. The intermediate capsule compartments are more suitable for a modified release compartment, as dissolution or disruption of the end compartments can occur, without disturbance of these intermediate compartments, before the intermediate compartments are disrupted or dissolved.

The solid sub-units are more suitable as sustained release sub-units, because the dissolution of the matrix polymer is likely to occur more slowly than the disruption of the thin wall of a capsule compartment. The hollow bore of unit 313 (FIG. 8B) gives the solid unit 313 a dissolution rate tending toward first-order dissolution kinetics.

Each of the sub-units 12, 13, 14, 22, 23, 24, 32, 33, 34, 35 may contain the same or different drug substance and/or formulation. This may for example be in the form of powder, granulates, or other solid forms. Alternatively the capsule compartments 12, 14, 22, 34 may contain liquid, gel etc. formulations (not shown). The end sub-unit 35 may contain a drug substance or alternately may simply comprise a solid polymer cap devoid of drug substance.

Figure 13:
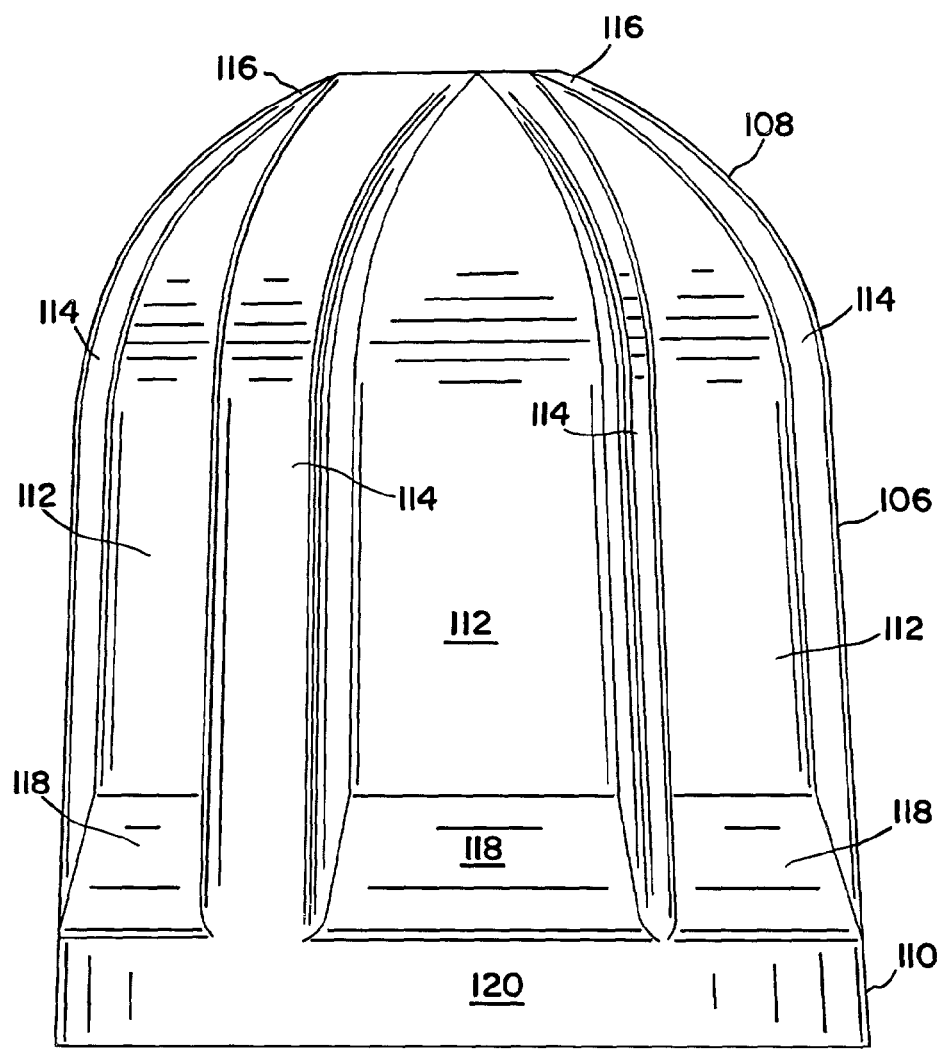
FIG. 13 is an elevational view of an injection-molded paneled shell in accordance with the invention.
Figure 14:
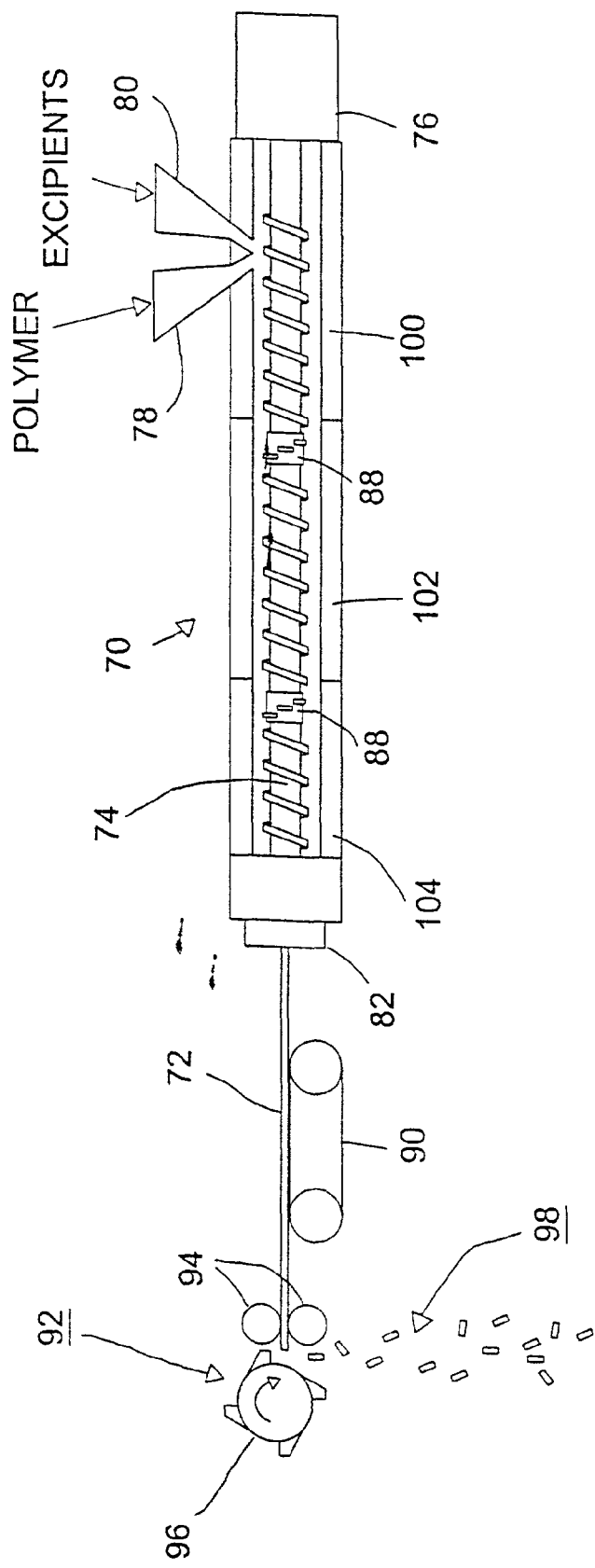
FIG. 14 is a schematic diagram illustrating the hot-melt extrusion and pelletizing apparatus for producing pellets for injection molding.

As shown in FIG. 13, a preferred capsule shell, having the advantages of thin walls for quick dissolution, but avoiding the deficiencies of excessively thin walls, is composed of a plurality of thin panels separated by reinforcing ribs. As seen in FIG. 13, the capsule is composed of three principal sections, a side wall 106, which is generally frusto-conical in shape, a generally hemispherical dome 108 and an annular rim 110. (The term "frusto-conical," as used herein, unless otherwise qualified, includes a cylindrical shape, i.e., a frustum having a zero taper.)

The side wall 106 is composed of a plurality of thin-walled panels 112 with reinforcing ribs 114, integrally formed on the exterior of the side wall 106, interposed between adjacent panels. The ribs may extend part way over the dome 108, and preferably taper gradually in thickness at 116 so that they merge smoothly with the peak of the dome. The ribs can be of various widths, as shown.

At least part 118 of the outer surface of the annular rim 110 is preferably in the form of a tapered, frusto-conical surface 118, and optional part 120, which is the outermost extending part of the rim 110 may be cylindrical. Part 110 extends outward from the lower part of wall 106 by a distance preferably equal to the thickness of the ribs at their lower ends, so that the ribs, which are connected to the tapered part 118, merge smoothly with the annular rim.

The capsule shell having the construction as shown in FIG. 13 can be used as a component of a single dosage capsule as well as a component of a multiple dosage form as depicted in FIGS. 8A-12. It has the advantage that its walls panels can be extremely thin, e.g., in the range of about 0.2 to 0.3 mm, for quick dissolution, but is resistant to distortion and breakage by virtue of its reinforcing ribs. In the preferred embodiment depicted in FIG. 13, the capsule shell configuration has no sharp edges or other external parts that could cause difficulty in handling or swallowing.

For purposes herein representative examples of polymers suitable for injection molding into single or multicomponent dosage forms and for use in pharmaceutical applications, include, but are not limited to, poly(ethylene) oxides (PEO), polyethylene glycol's (PEG), mixtures of PEG's and PEO's, polyvinyl alcohol (PVA), polyvinyl acetate, povidone (polyvinyl pyrrolidone), cellulose derivatives such as carboxymethyl cellulose, methyl cellulose, ethylcellulose, hydroxyethyl cellulose, hydroxypropylcellulose, hydroxyethyl methylcellulose, hydroxypropylmethyl cellulose (HPMC), hydroxypropylmethyl cellulose phthalate, cellulose acetate phthalate, noncrystalline cellulose, starch and its derivatives such as hydroxyethyl starch, sodium starch glycolate, natural polymers (such as polysaccharides like pullulan, carrageenan, xanthan, chitosan or agar gums), polyacrylates and poly(meth)acrylates, and its derivatives such as the Eudragit family of polymers available from Roehm Pharma, poly(alpha-hydroxy acids) and its copolymers such poly(caprolactone), poly(lactide-co-glycolide), poly(alpha-aminoacids) and its copolymers, polyglycolysed glycerides (such as Gelucire® 44/14, Gelucire® 50/02, Gelucire® 50/13 and Gelucire® 53/10), carboxyvinyl polymers (such as Carbopols), and polyoxyethylene-polyoxypropylene copolymers (such as Poloxamer 188™); and combinations or mixtures thereof.

Also potentially suitable for use herein are the polymers poly(orthoesters), polyphosphazenes, poly(phosphoesters), and polyanhydrides, and combinations or mixtures thereof may also be suitable for use herein.

Additionally, hyaluronic acid, alginates, carragenen, collagen, gelatin, and albumen may also be suitable for injection molding herein, either alone or in combination with another polymeric blend. It is recognized that the ultimate choice of polymers if not previously approved by the regulatory agencies of the world, are in the category of generally recognized as safe (GRAS) approved. Ultimately, if the polymer does not dissolve to release the contents of the component or sub-unit, the component may contain pore-forming reagents to allow the contents of the gastro-intestinal tract to enter the sub-unit and dissolve the active agent(s) therein. In such a capacity the sub-unit or dosage form will act more as a delivery device, and not as a capsule or controlled release modifying reagent. It is recognized that the choice of polymer will depend upon the desired outcome and the regulatory agency under which approval is being sought.

More suitably, methacrylic acid copolymers (such as Eudragit E®, Eudragit E100® Eudragit® L and/or Eudragit® S), poly(meth)acrylate copolymers, such as Eudragit® 4135F, and ammonium methacrylate copolymers (such as Eudragit® RL and/or Eudragit® RS), are suitable for injection molding. The group of poly(meth)acrylate copolymers, such as Eudragit® 4135F are a preferred aspect of this invention.

Eudragit E100 is also referred to as butylmethacylat-(2-dimethylaminoethyl)-methacrylat-methylmethacylat-co-polymer (1:2:1), is based on (2-dimethylaminoethyl)methacrylate, butyl methacrylate and methyl methacrylate having a mean molecular weight of about 150,000. It contains not less than 20.8 and not more than 25.5% dimethylaminoethyl groups in the dry substance.

Acrylic and/or methacrylic acid-based polymers which are soluble in intestinal fluids and which can be formed into capsules are for example disclosed in U.S. Pat. No. 5,705,189 (Roehm GmbH) the content of which is incorporated herein by reference in its entirety. These poly(meth)acrylate copolymers were extrudable and injection molded into capsule half's wherein the ratio of acrylic and/or methacrylic acid was generally 20% w/w or more off the copolymer (Examples 1-8). In these Examples, glycerol monosterate was added on a 3-5% wt base of the polymer as a mold-releasing agent.

A particular polymer disclosed in U.S. Pat. No. 5,705,189, emulsion E2 (column 6, line 10) being a copolymer of methacrylic acid, methyl methacrylate and methyl acrylate (suitably in a ratio of 10:25:65) has been found to be a preferred polymer for use in the present invention. This ratio of components is also known as Eudragit ® 4135F, and is a solid product obtained from Eudragit FS 30D, and as noted above is available from Roehm Pharma, Germany. However, it has been found that the unblended polymer alone is not suitable for injection molding, but must be blended in accordance with the teachings herein to produce suitable injection molded, non-distorted, unwarped capsule/sub-unit components for assembly into either single capsule or multicompartment dosage forms.

For the polymer E 4135F, at least one lubricant and one dissolution modifying agent are necessary to achieve quality, non-distortion molded components which readily release from the injection molds. The polymers exemplified in U.S. Pat. No. 5,705,189 all have increased viscosity's relative to the blended compositions as used in the this invention.

Therefore, one aspect of this invention is the novel blending of excipients to render this polymer suitable for injection molding into capsules and multi-compartmental units. A preferred polymer is a material that preferentially dissolves or disintegrates at different points in the digestive tract. As noted above, such polymers include the known acrylic and/or methacrylic acid-based polymers, which are soluble in intestinal fluids, e.g. the Eudragit™ series of commercially available polymers. Examples of these include Eudragit E™, such as Eudragit E 100™, which preferentially dissolves in the more acid pH of the stomach, or enteric polymers such as Eudragit L™ and/or Eudragit S™ which preferentially dissolve in the more alkaline pH of the intestine.

Other preferred polymers also include polymers which are insoluble but hydrate at a controllable rate, e.g. a predetermined rate in the digestive tract, such as Eudragit RL™, e.g. Eudragit RL 100™, and/or Eudragit RS™ e.g. Eudragit R100™, and/or blends of such Eudragit™ polymers. A suggested blend of polymers would be the combination of RL and RS with the necessary glidants and excipients.

The polymer Eudragit 4135F™ dissolves only above pH 7, e.g. in the colon and so is suitable for formulation as a sustained release component. In contrast, as noted, the polymer Eudragit E100™ dissolves in acid as so is suitable for use as an immediate release component.

Most of these pharmaceutically acceptable polymers are described in detail in the Handbook of Pharmaceutical excipients, published jointly by the American Pharmaceutical association and the Pharmaceutical society of Britain.

Preferably, the polymeric carriers are divided into three categories: (1) water soluble polymers useful for rapid dissolve and immediate release of active agents, (2) water insoluble polymers useful for controlled release of the active agents; and (3) pH sensitive polymers for pulsatile or targeted release of active agents. It is recognized that combinations of both carriers may be used herein. It is also recognized that several of the poly(meth)acrylates are pH dependent for the solubility and may fall into both categories.

One aspect of the present invention is the novel blending of components which has the ability to render the poly(meth)acrylates, such as 4135F, which are pH dependent independent of this characteristic. They are no longer governed by the pH of the solution, i.e. the gastric tract, but are time/controlled release dependent instead, which determination is based upon the addition of the swellable solids and surfactants which will be described in further detail herein.

Water soluble polymers generally include but are not limited to, poly(ethylene oxide), polyvinyl alcohol, polyvinyl pyrrolidone, hyaluronic acid, alginates, carragenen, cellulose derivatives such as carboxymethyl cellulose sodium, hydroxyethyl cellulose, hydroxypropylcellulose, hydroxypropylmethyl cellulose, hydroxypropylmethyl cellulose phthalate, cellulose acetate, cellulose acetate propionate, cellulose acetate phthalate, starch and its derivatives such as hydroxyethyl starch, sodium starch glycolate, dextrin, chitosan and its derivatives, albumen, zein, gelatin, and collagen.

Water insoluble polymers generally include but are not limited to, polyvinyl acetate, methyl cellulose, ethylcellulose, noncrystalline cellulose, polyacrylates and its derivatives such as the Eudragit family of polymers available from Rohm Pharma (Germany), poly(alpha-hydroxy acids) and its copolymers such as poly($\epsilon$-caprolactone), poly(lactide-co-glycolide), poly(alpha-aminoacids) and its copolymers, poly (orthoesters), polyphosphazenes, poly(phosphoesters), and polyanhydrides. A preferred polymer for use herein is the poly methacrylate, Eudragit 4135F present in an amount of 20 to 90% w/w, preferably 50 to 90% w/w.

These pharmaceutically acceptable polymers and their derivatives are commercially available and/or are prepared by techniques known in the art. By derivatives it is meant, polymers of varying molecular weight, modification of functional groups of the polymers, or co-polymers of these agents, or mixtures thereof.

Further, two or more polymers may be used in combination to form blends having the desired characteristics, such as enhanced flow, flexibility in molding or desired drug release profile.

It is recognized that polymeric composition which are first melted in a melt extrusion process, may also contain additional additives or excipients to assists in melt flow, strength, brittleness, and other molding characteristics, these additional excipients include but are not limited to, plasticizers, absorption enhancers, additional surfactants, flavouring agents, dyes, etc.

While the compositions herein may be molded in varying wall-thickness, it is preferably that capsules or components have a wall-thickness of about 0.3 to about 0.8 mm. However, dissolution performance will more appropriately tailor the wall thickness depending upon the release profiles desired. Increases in wall thickness may be necessary to reduce warping of the components, or modification of the additional excipients in addition to this may be necessary.

The polymer material(s) may include other substances to modify their properties and to adapt them to various applications, including but not limited to surfactants, absorption enhancers, lubricants, plasticizers, dissolution modifying agents, processing aids, colouring agents, flavouring agents and sweetening agents. Incorporation of a surfactant into the formulation may be necessary or desired to lower the viscosity and surface tension of the formulation/blend, however, in higher amounts it may adversely effect the quality of the resulting dosage form. The surfactant selection may be guided by HLB values but is not necessarily a useful criterion. While HLB surfactants have been utilized herein, such as Tween® 80 (HLB=10), Pluronic F68 (HLB=28), and SDS (HLB>40), lower HLB value surfactants, such as Pluronic F92 and F127 may also be used. Pluronic, made by BASF, USA has a synonym of POLOXAMER. Pluronic F68 for instance has a molecular weight of 8,400. Pluronic F127 has a molecular weight of 12,600. Pluronics are polyoxypropylene-polyoxyethylene block copolymers.

A surfactant may also be called an oligomeric surface modifier and includes, but is not limited to: Pluronics® (block copolymers of ethylene oxide and propylene oxide, and are also referred to as polyoxypropylene-polyoxyethylene block copolymers); lecithin, Aerosol OT® (sodium dioctyl sulfosuccinate), sodium lauryl sulfate, Polyoxyl 40™ hydrogenated castor oil, polyoxyethylene sorbitan fatty acid esters, i.e., the polysorbates such as Tween®, such as Tween 20, 60 & 80, the sorbitan fatty acid esters, i.e., sorbitan monolaurate, monooleate, monopalmitate, monosterate, etc. such as Span® or Arlacel®, Emsorb®, Capmul®, or Sorbester®, Triton X-200, polyethylene glycol's, glyceryl monostearate, Vitamin E-TPGS® (d-alpha-tocopheryl polyethylene glycol 1000 succinate), sucrose fatty acid esters, such as sucrose stearate, sucrose oleate, sucrose palmitate, sucrose laurate, and sucrose acetate butyrate, etc.; and combinations and mixtures thereof. Preferred surfactants are Vitamin E-TPGS®, sodium lauryl sulfate, sucrose fatty acid esters, lecithin, and the Pluronic groups.

Suitably, the formulation will contain from about 0 to about 10% w/w surfactant(s). A preferred surfactant is sodium lauryl sulfate, also referred to as sodium dodecyl sulfate (SDS) or a block copolymers of ethylene oxide and propylene oxide, or a mixture thereof. Preferably, if SDS or a block copolymers of ethylene oxide and propylene oxide is used in the formulation, they are present in an amount less than 2% by weight, more preferably <1% w/w.

A preferred use of the surfactant in combination with the E4135F formulations is to achieve a pulse release of the contents of the capsule such as in a 2-8 hour, more preferably a 3-4 and 6-8 hour windows. Use of SDS appears to produce a capsule shell having these desired release characteristics. Use of other surfactants, such as the Pluronic group may affect the release time to give a later detachment, such as for a late release/pulse.

The polymeric carriers or the second oligomeric surface modifiers, if appropriately chosen, may themselves act as absorption enhancers. Suitable absorption enhancers for use herein, include but are not limited to, chitosan, lecithin, lectins, sucrose fatty acid esters such as the ones derived from stearic acid, oleic acid, palmitic acid, lauric acid, and Vitamin E-TPGS, and combinations or mixtures thereof. Suitably, the absorption enhancers are present in a range of about 0-20% w/w.

Plasticizers are employed to assist in the melting characteristics of the composition. Exemplary of plasticizers that may be employed in this invention are triethyl citrate (TEC), triacetin, tributyl citrate, acetyl triethyl citrate (ATEC), acetyl tributyl citrate (ATBC), dibutyl phthalate, dibutyl sebacate (DBS), diethyl phthalate, vinyl pyrrolidone glycol triacetate, polyethylene glycol, polyoxyethylene sorbitan monolaurate, propylene glycol, or castor oil; and combinations or mixtures thereof. The polymeric material will determine which plasticizer is suitable for use. For instance, triacetin is not preferred for use with E100 or 4135F at levels of about 5% but may be suitable for use with Eudragit RS or RL, or PVA. Suitably, the plasticizer is present in an amount of about 0 to about 20% w/w. Preferably, from about 0 about 5% w/w. An important aspect of the present invention is the ability to form an injection molded shell of a Eudragit 4135F formulation without the addition of a plasticizer such as those noted above.

Dissolution modifying agents, or substances which assist in release modification alter the erosion and/or swelling characteristics of the shell. Many different classes of agents may be used, such as the known disintegrants represented by "Explotab" (sodium starch glycollate), "Kollidon-CL", (cross-linked PVP), Kollidon VA 64 (copovidone) commercially available from BASF, Starch 1500, swelling agents such as polyvinyl pyrrolidone (PVP, also know as POVIDONE, USP), manufactured by ISP-Plasdone or BASF-Kollidon, primarily Grades with lower K values (K-15, K-25, but also K-30 to K-90), cellulosic derivatives such as hydroxypropyl methyl cellulose (HPMC), wicking agents such as low molecular weight solutes, e.g. mannitol, lactose, and starch; inorganic salts such as sodium chloride (typically at 5-10%).

Kollidan VA 64, or copovidone, is also known as copolyvidone, copovidonum, copovidone or copovidon, is ratio of two monomers, vinylpyrrolidone and vinyl acetate.

More specifically, the class of agents known as swellable solids for use as dissolution modifying agents, includes but is not limited to poly(ethylene)oxide, the cellulosic derivatives, such as ethyl cellulose and cellulose acetate phthalate; hydroxypropylcellulose (HPC), especially at lower molecular weights, e.g., KLUCEL EF and LF grades, available from Aqualon, hydroxypropylmethyl cellulose, and other hydroxyalkylcellulose derivatives. Suitably, the swellable solids used as dissolution modifying excipients are in the range of about 5% to about 70% w/w, preferably about 10 to 50%. Dependent upon whether an immediate or a longer dissolution rate profile is indicated, the amount of HPC, if so used, will vary. If an immediate dissolution rate is preferred than preferably there is about 40 to 70% w/w HPC present. If a modified pulse release rate profile is preferred, than the amount of HPC will be decreased, and suitably additional dissolution modifying excipients in combination with HPC will be used. Therefore the amount of HPC may vary from about 5 to 70% w/w. In combination, HPC is likely to present from 10 to 40% w/w, preferably <30% w/w.

Other suitable dissolution modifying excipients include, but are not limited to the class of non-reducing sugars, such as xylitol, or mannitol, present in the range of about 2.5 to 15% w/w. Also included are the class of water soluble fillers, such as lactose, suitably present in the range of about 5 to 20%.

Another group of suitable dissolution modifying excipients are the agents generally referred to as disintegrants, such as sodium starch glycolate, croscarmellose sodium NF (Aci- Di-Sol® produced by FMC), copovidone, and crospovidone (cross-linked polyvinyl pyrrolidone); and combinations or mixtures thereof. Suitably, the class of disintegrants are present in the range of about 10 to 40%, more preferably about 20 to 30% w/w. It is recognized that the one of more classes of dissolution modifying excipients may be used alone, or in combination as mixtures with each other, resulting in a range of about 2.5 to 70% w/w. One such combination is croscarmellose sodium and sodium starch glycolate. Another is the combination of hydroxypropylcellulose and lactose. Preferably hydroxypropyl-cellulose is used in amounts from 10 to 70% w/w, more preferably 40 to 70% and lactose in ranges of about 0 to 10%, preferably 5% w/w.

Additional regents, generally classified as processing aids, include strengthening agents, such as talc. Suitably, the processing aids are present from about 0 to about 10% w/w.

Suitable mold processing lubricants or glidants for use herein, include but are not limited to, stearyl alcohol, stearic acid, glycerol monosterate (GMS), talc, magnesium stearate, silicon dioxide, amorphous silicic acid, and fumed silica; and combinations or mixtures thereof. This functions primarily as a flow promoter for the composition. A preferred lubricant is stearyl alcohol, or GMS. A commercial grade of stearyl alcohol, such as Crodacol S95 (Croda Oleochemicals) is preferred for use herein. The material should be suitable for milling. Suitably, the amount of lubricant present in the formulation is from about 0 to about 30% w/w, preferably from about 10 to about 25% w/w, and more preferably, 10 to 15% w/w.

Stearyl alcohol has the advantage that it acts as a mold processing lubricant but causes no mold distortion, i.e. crumpling of the multidosage compartment shell when the hot soft shell is taken out of the mold, which might result from a lubricant which made the blend flow better. An another alternate material also useable as lubricant/flow promoters is lecithin (a natural product). Suitably, the lubricants for use herein do not introduce any metal ion contamination.

A preferred aspect of the invention is the combination of a stearyl alcohol, a swellable solid, and a surfactant with the polymer, Eudragit 4135F. Suitably one surfactant is SDS at 2% w/w or less, more preferably 1% or less, Pharmacoat 603 or HPMC 5% w/w, and 20% w/w swellable solids such as 10% Explotab and/or 10% AcDiSol.

The final products of this invention, i.e. the capsules, and or components or sub-units may additionally include materials in the polymer materials of which they are made to enhance the ease with which they can be welded together. The sub-units may additionally be provided with constructional features and/or include materials in the polymer materials of which they are made to enhance the ease with which they can be welded together, e.g. opacifier materials such as carbon (e.g. 0.2-0.5%), iron oxides or titanium dioxide (e.g. 0.5-1.0%) to help the polymer to absorb laser energy. Such opacifier materials are generally regarded as safe.

For example each of a plurality of sub units, e.g. of the capsule compartments, solid sub-units, or combinations thereof may comprise the same or different polymer(s). For example each of a plurality of sub units, e.g. of capsule compartments, solid sub-units, or combinations thereof may comprise the same or different drug substance. For example each sub-unit may contain the same drug substance but release the contents into the gastro-intestinal tract of the patient at a different rate, at different times after administration to the patient or at different places in the patient's gastro-intestinal system. Alternatively each sub-unit may contain a different drug substance, each of which may be released at the same or a different rate or time after administration or place in the patient's gastro-intestinal system.

For example two or more sub-units, e.g. two capsule compartments, may each contain different drug substances, and/or different drug substance formulations, and/or the same drug in different formulations, so that a combination of two or more drug substances or formulations may be administered to a patient.

The dosage form of this invention enables the assembly together of sub-units which differ in their drug content and/or drug content release characteristics to provide a dosage form tailored to specific administration requirements.

The dimensions and shape of each of the sub-units and hence of the overall assembled dosage form may be determined by the nature and quantity of the material to be contained therein and the intended mode of administration and intended recipients. For example a dosage form intended for oral administration may be of a shape and size similar to that of known capsules intended for oral administration.

The dosage form is particularly suitable for presentation as an oral dosage form containing one or more drug substances suitable for oral administration, and appears to be suitable for all types of such drug substance.

The drug substance(s) contained in any capsule compartment may be present in any suitable form, e.g. as a powder, granules, compact, microcapsules, gel, syrup or liquid provided that the capsule compartment wall material is sufficiently inert to the liquid content of the latter three forms. The contents of the compartments, e.g. drug substances, may be introduced into the compartments by standard methods such as those used conventionally for filling capsules, such as dosating pins or die filling.

The sub-units may differ from each other in their drug content release characteristics, and this may be achieved in various ways. For example one or more solid sub-units and/or capsule compartments may be substantially immediate release, i.e. releasing their drug contents substantially immediately upon ingestion or on reaching the stomach. This may for example be achieved by means of the matrix polymer or the capsule compartment wall dissolving, disintegrating or otherwise being breached to release the drug content substantially immediately. Generally, immediate-release sub-units are preferably provided by being capsule compartments.

For example one or more solid sub-units and/or capsule compartments may be sustained-release sub-units. Preferably these are solid sub-units, as a bulk matrix of polymer is likely to dissolve or disperse more slowly to release its drug content that a thin walled capsule.

For example one or more solid sub-units and/or capsule compartments may be pulsed-release sub-units for example releasing their drug content at a specific predetermined point in a patient's gastro-intestinal system. This may be achieved by the use of polymer materials which dissolve or disperse only at defined pH environments, such as the above mentioned Eudragit® polymers. For instance, E100 is acid labile.

For example in the above-described capsule compartment-linker-capsule compartment dosage form one capsule compartment may be effectively immediate release and the other may be sustained, delayed or pulsed release. To achieve this for example one capsule compartment may be made of polymer materials which cause the capsule compartment to release its drug content in the stomach or upper part of the digestive tract, and the linker (acting as a closure for the second compartment) and the second compartment itself may be made of materials e.g. the above described enteric polymers, which release their drug content only in the intestinal environment.

Determination of the time or location within the gastro-intestinal tract at which a sub-unit releases its drug substance content may be achieved by for example the nature of the sub-unit material, e.g. a solid sub-unit matrix polymer or a capsule compartment wall material, or in the case of an end compartment which is closed by a closure, by the nature of the closure material. For example the wall of different, e.g. adjacent, compartments may be made of polymers which are different or which otherwise differ in their dissolution or disintegration characteristics so as to endow different compartments with different drug release characteristics. Similarly for example the polymer matrix material of different, e.g. adjacent, solid sub-units may be made of polymers which are different or which otherwise differ in their dissolution or disintegration characteristics so as to endow different solid sub-units with different drug release characteristics.

For example the matrix, wall or closure material may be a polymer which dissolves or disperses at stomach pH to release the drug substance in the stomach. Alternatively the wall material of different compartments may differ so that different compartments have different release characteristics.

For example a solid sub-unit or a capsule compartment may have respectively a matrix or a wall or a closure comprising an enteric polymer which dissolves or disperses at the pH of the small or large intestine to release the drug substance in the intestine. Suitable such polymers have been described above, for example, with reference to U.S. Pat. No. 5,705, 189.

Additionally or alternatively the wall material may differ in thickness between compartments so that thicker walled compartments disrupt more slowly than thinner walled compartments.

Additionally or alternatively the compartment walls or the closure may have areas or points of weakness which preferentially dissolve and may thereby determine the time of onset and/or rate of release of the drug substance content. For example such points of weakness may comprise holes, e.g. small holes, e.g. laser-drilled holes in the compartment wall or the closure, these holes being closed and/or covered with a film of a polymer material that dissolves at a pre-determined point in the digestive tract, for example an enteric polymer material. For example such points of weakness may comprise thinned parts in a capsule compartment wall formed during the molding operation in which the capsule compartment is formed.

The sub-units may additionally or alternatively have surface or other constructional features that modify their drug release characteristics. For example solid sub-units may be provided with internal cavities or channels to create a large surface area. For example solid sub-units may be in the form of hollow cylinders, donuts, or toroids, which shapes are known to tend towards first-order dissolution or erosion in liquid media and correspondingly to tend toward first-order release of drug content dispersed therein.

Pharmaceutically acceptable agents, actives or drugs as used herein, is meant to include active agents having a pharmacological activity for use in a mammal, preferably a human. The pharmacological activity may be prophylactic or for treatment of a disease state.

As used herein the term's "active agent", "drug moiety" or "drug" are used interchangeably.

Water solubility of an active agent is defined by the United States Pharmacoepia. Therefore, active agents which meet the criteria of very soluble, freely soluble, soluble and sparingly soluble as defined therein are encompassed this invention.

Suitable drug substances can be selected from a variety of known classes of drugs including, but not limited to, analgesics, anti-inflammatory agents, anthelmintics, anti-arrhythmic agents, antibiotics (including penicillin's), anticoagulants, antidepressants, antidiabetic agents, antiepileptics, antihistamines, antihypertensive agents, antimuscarinic agents, antimycobactefial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, PDE IV inhibitors, NK3 inhibitors, CSBP/RK/p38 inhibitors, antipsychotics, vasodilators and xanthines.

Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989, the disclosure of which is hereby incorporated herein by reference in its entirety. The drug substances are commercially available and/or can be prepared by techniques known in the art.

The polymeric blends can be preferably selected from known pharmaceutical polymers. The physico-chemical characteristics of these polymers, as well as the thickness of the ultimate injection molded component, will dictate the design of the dosage form, such as rapid dissolve, immediate release, delayed release, modified release such as sustained release, controlled release, or pulsatile release. etc.

The polymer blends are made by well-known methods for producing hot melt extrusions in which the selected ingredients are fed into a feed hopper of an extrusion machine. Suitable well known equipment is readily available for producing a hot melt extrusion of the blends herein.

As shown in FIG. 11, a hot melt extruder 70 is shown producing a strand 72 consisting of a homogeneous mixture of polymer (Eudragit 4135F) and an excipient composition. The extruder is a twin-screw extruder (one screw 74 being shown). The screws are driven by a motor 76. The polymer and excipient composition are introduced respectively through hoppers 78 and 80. The hoppers feed the polymer and excipient simultaneously, and at substantially the same location, to the interior of the barrel of the extruder at a location near the end of the extruder remote from die 82. The introduction of both the polymer and the excipient composition at substantially the same location ensures a high degree of homogeneity in the composition of the extruded strand 72, which as mentioned previously is important especially in the case of a thin-walled capsule compartment. Mixing elements 88 are provided at intervals along the screws to knead the material as it is propelled through the barrel of the extruder.

The strand 72 is conveyed by belt 90 toward a pelletizer 92 which comprises a pair of rolls 94 and a rotating cutter 96. The pelletizer cuts the strand 72 into pellets 98, which are collected and conveyed to an injection molder (not shown).

In the hot melt extruder, the polymer-excipient mixture is gradually heated by heating coils shown schematically at 100, 102 and 104. The die is preferably separately heated. The heating coils and the die heater are preferably set so that the temperature in the hot melt extruder increases gradually from a relatively low temperature, e.g. 50° C., at the location at which the polymer and excipient composition are introduced to a die temperature in the range of about 110° C. to about 135° C. The highest temperature is preferably maintained at a level not exceeding 125° C., although a temperature of 135° C. can be tolerated by a composition comprising poly(meth) acrylate copolymer, dissolution modifying excipients, lubricants and optionally processing aids and surfactants.

Figure 15:
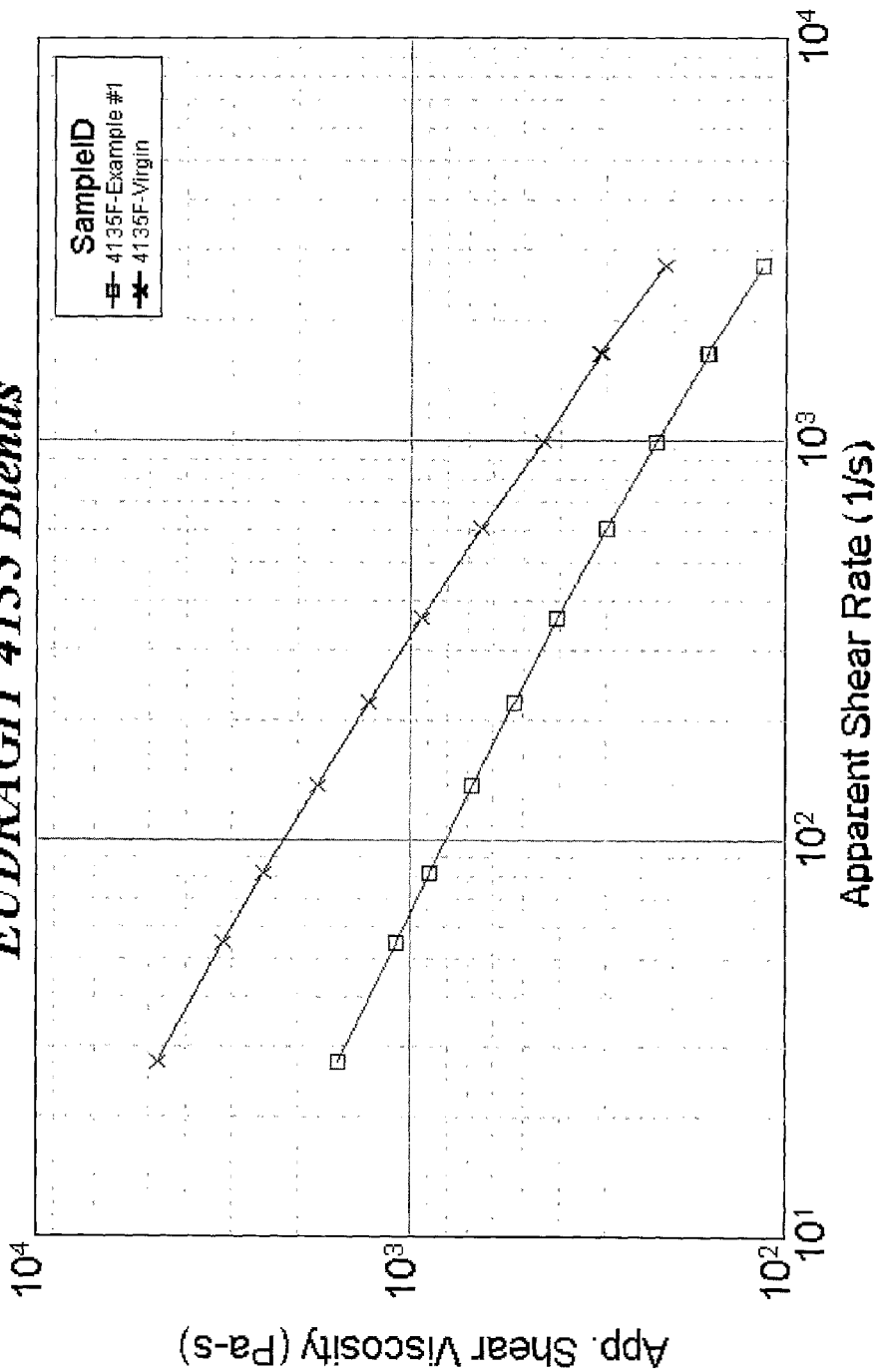
FIG. 15 is rheology plot comparing Eudragit 4135 base polymer to Example 1 blended polymeric formulation.

As shown in FIG. 15, a rheology plot comparing Eudragit 4135F base polymer with the formulation of Example 1 demonstrates that the addition of hydroxypropylmethycellulose, lactose and stearyl alcohol, as processing aids reduces viscosity at a given shear rate and allows components to be moulded at temperatures lower that their degradation rate, causing no problems with degradation.

Fast Release/Pulse Capsules or Components

For production of an early release/pulse capsule or component in a multidosage capsule, (such as a 2-4 hour window), the polymer Eudragit 4135F (Röhm), may be extruded into a thin walled component shell (such as those indicated herein), by blending with several excipients as noted herein. As will be seen by the experimental section, formulation with a surfactant and a swellable solid will produce a stable, injection molded component which can be reliably reproduced and injected from the mold with reduced, or no warpage of the shell.

Experiments with Klucel HPC at various percentages, ranging from 10 to 70% have been formulated and tested for the variance in dissolution times. Formulations containing 40 to 70% Klucel have been found to have similar dissolutions times (<2 hours) in both simulated gastric fluid and simulated intestinal fluids. Dissolutions times for formulations containing 10 to 30% Klucel are longer and more variable indicating that a 40% level of Klucel is necessary to provide reproducible release profiles.

Slow/Delayed Release/Pulse Capsules or Components

For production of a slow release, or a delayed release capsule or component in a multidosage capsule, the polymer Eudragit 4135F (Röhm), as noted above is preferred. The principal problem with Eudragit® 4135F in its unformulated state is its high dissolution time, in excess of 30 hours in aqueous media e.g. in SIF (simulated intestinal fluid). Therefore, to improve its dissolution time the polymer is blended with one or more hydrophilic excipients. This will enhance the absorption of water by the Eudragit 4135F polymer, and so accelerate the rate at which the blended polymer swells on absorption of water. As noted by the Experimental section herein, a dissolution modifying excipient, preferably a swellable solid excipient and optionally a second dissolution modifying excipient, such as a disintegrant, a lubricating agent, and if desired a surfactant, will produce a stable, injection molded component which can be reliably reproduced and injected from the mold with reduced, or no warpage of the shell.

A preferred multicomponent dosage form is that disclosed in PCT/EP00/07295, filed Jul. 27, 2000, published as WO 01/08666 on Feb. 8, 2001, the contents of which are incorporated by reference herein in its entirety. The multicomponent dosage form of this application preferably uses an ultrasonic weld to seal to components together. The Eudragit 4135F will open to release its contents by swelling in the region of the ultrasonic weld, which causes separation at the weld or release through erosion at a thinner (paneled) are of the shell.

As noted above, a number of dissolution modifying agents, such as hydrophilic excipients may be used to assist in the swelling of the shell, excipients such as PEG (polyethylene glycol), e.g. PEG 4000, 6450, 8000, produced by Dow and Union Carbide in combination with the 4135F has been found to act as a plasticiser and resulted in mold distortion. Gelucire (a fatty acid PEG ester) may cause a similar problem, due to traces of PEG in the Gelucire.

Preferably, the hydrophilic excipient is one which does not melt at the extrusion temperature, e.g. the lactose, inorganic salts, HPC, HPMC, such as Pharmacoat 603 (an HPMC with a glass transition temperature 175° C.). Copovidone has been found to be a preferred ingredient for use herein with Eudragit F4135, along with HPMC, and other cellulosics or swellable agents. As noted, these swellable solids are available commercially in a number of grades by molecular weight, for examples 95K, or 80K grades of HPC. A change in the molecular weight of HPC, for instance, should retain the ability to hydrate the shell, but the hydration rate may be slower, i.e. the rate of expansion will be reduced. Hence, a longer dissolution time of the shell and release of the components therein may result. Experiments with Klucel HPC at various percentages, ranging from 10 to 70% have been formulated and tested for the variance in dissolution times. Formulations containing 40 to 70% Klucel have been found to have similar dissolutions times. Dissolution times for formulations containing 10 to 30% Klucel are expected to behave similarly.

Additionally, inclusion of a lubricant, such as stearyl alcohol is also preferred. It has been found to enhance flow, i.e. and is used preferably at a 10 to 20%, more preferably at 12 to 15% w/w. It is also found that higher proportions of stearyl alcohol increase the flowability so as to enable molding of thinner walls.

Spacer Components

This is the plug like linker that closes and connects the two end compartments of the capsules (such as immediate release and slow/sustained release compartments). This can be made of the same polymer blend (4135F blend) as the slow/delayed release components, etc., but can equally well be made of 4135F blended with a suitable lubricant, such as stearyl alcohol, but without other hydrophilic excipients. By not including the hydrophilic excipient in the spacer the opening of the slow/delayed release component will be improved because of the mismatch in water disturbance and thus differential swelling, of the slow/delayed release component and the spacer acting as a plug closure of the compartment.

Preferably, use of a delayed release polymer to form a slow/delayed release component or sub-unit which is part of a multicomponent dosage form, will provide for a means to release the contents of the sub-unit by failure of the weld, as the thin region of the end cap compartments which overlap the linker plug swells rapidly and will pull away from the adjacent spacer, thereby opening the contents of the sub-unit into the gastrointestinal fluids.

The capsule components of the present invention can be produced in accordance with the Description and the Examples herein. Example 1 provides for a general summary of the extrusion and moulding parameters used for Eudragit 4135F.

However, in general the extruder is preheated to the appropriate temperature, approximately a temperature of about 110-135° C., preferably 125° C. The injection moulder is preheated to the appropriate temperature, approximately a temperature of 120-140° C. across the screw/barrel and 140-

190° C., preferably 170° C. on the hot-tip/nozzle, which should be maintained throughout.

EXAMPLES

The invention will now be described by reference to the following examples, which are merely illustrative and are not to be construed as a limitation of the scope of the present invention. All temperatures are given in degrees centigrade; all solvents are highest available purity unless otherwise indicated.

Example 1

Manufacture of multicomponent pharmaceutical dosage forms with pharmaceutically acceptable polymeric compositions as described herein. Example 1 will describe a general process used to mold the various multicomponent capsules and appropriate sub-units. Additional pharmaceutical compositions are shown and described below.

| Item number | Material | % w/w |
|---|---|---|
| 1. | Copolymer of methacrylic acid, methyl acrylate and methylmethacrylate (Eudragit 4135) | 73.0 |
| 2. | Hydroxypropyl Methylcellulose (Pharmacoat 603) | 10.0 |
| 3. | Lactose monohydrate | 5.0 |
| 4. | Stearyl alcohol, milled | 12.0 |
| | Total | 100 |

Using a suitable blender mix together:
Item 2. Hydroxypropyl Methylcellulose (Pharmacoat 603)
Item 3. Lactose monohydrate
Item 4. Stearyl alcohol, milled
to form a homogeneous powder blend.

Set up a suitable co-rotating twin screw hot melt extruder with both a pellet feeder and a powder feeder together with strand cooling equipment and a pelletizer. Fit the selected mold in the injection molding machine. Example processing parameters are as follows:

| Extruder: | |
|---|---|
| Screw speed for a 19 mm extruder, or 16 mm extruder | 150 rpm (range 125-175 rpm) 200 rpm (100-300 rpm) on a |
| Temperature of zone 1 (feed zone) | 60° C. (range 30-75° C.) |
| Temperature of zone 2 | 115° C. (range 85-130° C.) |
| Temperature of zone 3 | 120° C. (range 90-135° C.) |
| Temperature of zone 4 | 125° C. (range 95-140° C.) |
| Temperature of zone 5 | 130° C. (range 100-145° C.) |
| Temperature of strand die | 135° C. (range 105-150° C.) |
| Pellet feeder | 1.6 kg/hour (0.7-2.1 kg/hour) |
| Powder feeder | 0.6 kg/hour (0.26-0.79 kg/hour) |
| Strand cooling equipment: | Appropriate for extrusion rate used |

Pelletiser: Appropriate for extrusion rate used
Injection molder: Appropriate injection/cooling times, temperature and injection pressure, dependent on machine type and pellet formulation.

Pre-heat the extruder to the appropriate temperature. Load the pellet feeder with the Copolymer of methacrylic acid, methyl acrylate and methylmethacrylate (Eudragit 4135F) and the powder feeder with the blend. Start the extruder screws rotating and then start the two feeders. Process the extruded strand along the cooling equipment into the pelletiser and collect the pellets formed.

Under operating conditions, it has been found the port opening before the die is open to atmospheric conditions to force out any water/vapor coming off the extrusion process. It has, however, been found that the 4135F formulations of the present invention do not appear to have any excessive moisture problems when injection molded.

Input appropriate machine settings and pre-heat the injection molder. Load the hopper with the pellets and mold the multi-components units.

Additional examples or embodiments of this example have been prepared, using the same process steps but with variant formulations as shown below.

| Example # | Formulation | (% w/w) |
|---|---|---|
| Example 2 | Eudragit 4135F | 75.0 |
| | Stearyl alcohol | 5.0 |
| | Ac-Di-Sol (croscarmellose sodium) | 20.0 |
| Example 3 | Eudragit 4135F | 75.0 |
| | Stearyl alcohol | 5.0 |
| | Explotab (sodium starch glycollate) | 20.0 |
| Example 4 | Eudragit 4135F | 85.0 |
| | Stearyl alcohol | 5.0 |
| | Xylitol | 10.0 |
| Example 5 | Eudragit 4135F | 75.0 |
| | Stearyl alcohol | 5.0 |
| | Ac-Di-Sol (crocarmellose sodium) | 10.0 |
| | Xylitol | 10.0 |
| Example 6 | Eudragit 4135F | 75.0 |
| | Stearyl alcohol | 5.0 |
| | Mannitol | 10.0 |
| | Explotab (sodium starch glycollate) | 10.0 |
| Example 7 | Eudragit 4135F | 65.0 |
| | Stearyl alcohol | 5.0 |
| | Mannitol | 10.0 |
| | Explotab (sodium starch glycollate) | 20.0 |
| Example 8 | Eudragit 4135F | 80.0 |
| | Stearyl alcohol | 5.0 |
| | Explotab (sodium starch glycollate) | 10.0 |
| | Lactose monohydrate | 5.0 |
| Example 10 | Eudragit 4135F | 85.0 |
| | Stearyl alcohol | 5.0 |
| | Lactose monohydrate | 10.0 |
| Example 11 | Eudragit 4135F | 75.0 |
| | Stearyl alcohol | 5.0 |
| | Lactose monohydrate | 20.0 |
| Example 12 | Eudragit 4135F | 80.0 |
| | Stearyl alcohol | 5.0 |
| | Explotab (sodium starch glycollate) | 5.0 |
| | Lactose monohydrate | 10.0 |
| Example 13 | Eudragit 4135F | 70.0 |
| | Stearyl alcohol | 5.0 |
| | Explotab (sodium starch glycollate) | 5.0 |
| | Lactose monohydrate | 20.0 |
| Example 14 | Eudragit 4135F | 75.0 |
| | Stearyl alcohol | 10.0 |
| | Mannitol | 7.5 |
| | Explotab (sodium starch glycollate) | 7.5 |
| Example 15 | Eudragit 4135F | 80.0 |
| | Stearyl alcohol | 5.0 |
| | Starch 1500 | 10.0 |
| Example 16 | Eudragit 4135F | 85.0 |
| | Stearyl alcohol | 5.0 |
| | Starch 1500 | 15.0 |
| Example 17 | Eudragit 4135F | 80.0 |
| | Stearyl alcohol | 5.0 |
| | Starch 1500 | 10.0 |
| | Lactose monohydrate | 5.0 |
| Example 18 | Eudragit 4135F | 85.0 |
| | Stearyl alcohol | 5.0 |
| | Kollidon CL | 10.0 |
| Example 19 | Eudragit 4135F | 80.0 |
| | Stearyl alcohol | 5.0 |

-continued

| Example # | Formulation | (% w/w) |
|---|---|---|
|  | Explotab (sodium starch glycollate) | 10.0 |
|  | Lactose monohydrate | 5.0 |
| Example 21 | Eudragit 4135F | 85.0 |
|  | Stearyl alcohol | 5.0 |
|  | Sodium chloride | 5.0 |
|  | Lactose monohydrate | 5.0 |
| Example 22 | Eudragit 4135F | 85.0 |
|  | Stearyl alcohol | 5.0 |
|  | Klucel LF | 5.0 |
|  | Lactose monohydrate | 5.0 |
| Example 23 | Eudragit 4135F | 85.0 |
|  | Stearyl alcohol | 5.0 |
|  | Pharmacoat 603 | 5.0 |
|  | Lactose monohydrate | 5.0 |
| Example 24 | Eudragit 4135F | 80.0 |
|  | Stearyl alcohol | 10.0 |
|  | Pharmacoat 603 | 5.0 |
|  | Lactose monohydrate | 5.0 |
| Example 25 | Eudragit 4135F | 80.0 |
|  | Stearyl alcohol | 10.0 |
|  | Explotab (sodium starch glycollate) | 5.0 |
|  | Lactose monohydrate | 5.0 |
| Example 26 | Eudragit 4135F | 80.0 |
|  | Stearyl alcohol | 10.0 |
|  | Hypromellose phthallate | 5.0 |
|  | Lactose monohydrate | 5.0 |
| Example 27 | Eudragit 4135F | 80.0 |
|  | Stearyl alcohol | 10.0 |
|  | Low substituted hydroxypropylcellulose | 5.0 |
|  | Lactose monohydrate | 5.0 |
| Example 28 | Eudragit 4135F | 90.0 |
|  | Stearyl alcohol | 5.0 |
|  | Pharmacoat 603 | 5.0 |
| Example 29 | Eudragit 4135F | 90.0 |
|  | Stearyl alcohol | 5.0 |
|  | Lactose monohydrate | 5.0 |

Additional Examples have prepared in a similar manner to Example 1 above which include:

| Example # | Formulation | % w/w |
|---|---|---|
| Example 30 | Eudragit 4135F | 73.0 |
|  | Hydroxypropylmethyl cellulose (Pharmacoat 603) | 10.0 |
|  | Lactose (regular) | 5.0 |
|  | Glyceryl monostearate | 12.0 |
| Example 31 | Eudragit 4135F | 53.0 |
|  | Hydroxypropylmethyl cellulose (Pharmacoat 603) | 10.0 |
|  | Lactose (regular) | 5.0 |
|  | Hydroxypropylmethyl cellulose phthallate (HP55) | 20.0 |
|  | Stearyl alcohol | 12.0 |
| Example 32 | Eudragit 4135F | 20.0 |
|  | Hydroxypropylmethyl cellulose (Pharmacoat 603) | 10.0 |
|  | Hydroxypropylmethyl cellulose phthallate (HP55) | 20.0 |
|  | Stearyl alcohol | 12.0 |
| Example 33 | Eudragit 4135F | 68.0 |
|  | Hydroxypropylmethyl cellulose (Pharmacoat 603) | 10.0 |
|  | Lactose (regular) | 5.0 |
|  | Sodium dodecyl sulphate | 5.0 |
|  | Stearyl alcohol | 12.0 |
| Example 34 | Eudragit 4135F | 72.0 |
|  | Hydroxypropylmethyl cellulose (Pharmacoat 603) | 10.0 |
|  | Lactose (regular) | 5.0 |
|  | Sodium dodecyl sulphate | 1.0 |
|  | Stearyl alcohol | 12.0 |
| Example 35 | Eudragit 4135F | 71.0 |
|  | Hydroxypropylmethyl cellulose (Pharmacoat 603) | 10.0 |
|  | Lactose (regular) | 5.0 |
|  | Sodium dodecyl sulphate | 2.0 |
|  | Stearyl alcohol | 12.0 |
| Example 36 | Eudragit 4135F | 62.0 |
|  | Explotab | 20.0 |
|  | Lactose (regular) | 5.0 |
|  | Sodium dodecyl sulphate | 1.0 |
|  | Stearyl alcohol | 12.0 |

-continued

| Example # | Formulation | % w/w |
|---|---|---|
| Example 37 | Eudragit 4135F | 75.0 |
|  | Explotab | 10.0 |
|  | Stearyl alcohol | 5.0 |
|  | Lactose monohydrate | 10.0 |
| Example 38 | Eudragit 4135F | 72.0 |
|  | Explotab | 10.0 |
|  | Lactose (regular) | 5.0 |
|  | Sodium dodecyl sulphate | 1.0 |
|  | Stearyl alcohol | 12.0 |
| Example 39 | Eudragit 4135F | 62.0 |
|  | Ac-Di-Sol | 20.0 |
|  | Lactose (regular) | 5.0 |
|  | Sodium dodecyl sulphate | 1.0 |
|  | Stearyl alcohol | 12.0 |
| Example 40 | Eudragit 4135F | 62.0 |
|  | Explotab | 20.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 41 | Eudragit 4135F | 62.0 |
|  | Hydroxypropylmethyl cellulose phthallate (HP55) | 20.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 42 | Eudragit 4135F | 62.5 |
|  | Explotab | 20.0 |
|  | Hydroxypropylmethyl cellulose (Pharmacoat 603) | 5.0 |
|  | Sodium dodecyl sulphate | 0.5 |
|  | Stearyl alcohol | 12.0 |
| Example 43 | Eudragit 4135F | 62.0 |
|  | Ac-Di-Sol | 10.0 |
|  | Explotab | 10.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 44 | Eudragit 4135F | 67.0 |
|  | Ac-Di-Sol | 15.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 45 | Eudragit 4135F | 72.0 |
|  | Ac-Di-Sol | 10.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 46 | Eudragit 4135F | 77.0 |
|  | Ac-Di-Sol | 5.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 47 | Eudragit 4135F | 52.0 |
|  | Ac-Di-Sol | 15.0 |
|  | Explotab | 15.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 48 | Eudragit 4135F | 42.0 |
|  | Ac-Di-Sol | 20.0 |
|  | Explotab | 20.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 49 | Eudragit 4135F | 42.0 |
|  | Ac-Di-Sol | 20.0 |
|  | Explotab | 20.0 |
|  | Hydroxypropylmethyl cellulose (Pharmacoat 603) | 5.0 |
|  | Sodium dodecyl sulphate | 1.0 |
|  | Stearyl alcohol | 12.0 |
| Example 50 | Eudragit 4135F | 62.0 |
|  | Ac-Di-Sol | 5.0 |
|  | Explotab | 5.0 |
|  | Hydroxypropylmethyl cellulose (Pharmacoat 603) | 15.0 |
|  | Sodium dodecyl sulphate | 1.0 |
|  | Stearyl alcohol | 12.0 |
| Example 51 | Eudragit 4135F | 62.9 |
|  | Ac-Di-Sol | 10.0 |
|  | Explotab | 10.0 |

-continued

| Example # | Formulation | % w/w |
|---|---|---|
| | Hydroxypropylmethyl cellulose (Pharmacoat 603) | 5.0 |
| | Sodium dodecyl sulphate | 0.1 |
| | Stearyl alcohol | 12.0 |
| Example 52 | Eudragit 4135F | 62.0 |
| | Ac-Di-Sol | 10.0 |
| | Explotab | 10.0 |
| | Pluronic F-68 | 0.50 |
| | Sodium dodecyl sulphate | 0.50 |
| | Hydroxypropylmethyl cellulose (Pharmacoat 603) | 5.0 |
| | Stearyl alcohol | 12.0 |
| Example 53 | Eudragit 4135F | 61.0 |
| | Ac-Di-Sol | 10.0 |
| | Explotab | 10.0 |
| | Pluronic F-68 | 1.0 |
| | Sodium dodecyl sulphate | 1.0 |
| | Hydroxypropylmethyl cellulose (Pharmacoat 603) | 5.0 |
| | Stearyl alcohol | 12.0 |

Dissolution time in the simulated intestinal fluid, at a pH of 7.5 for 100% release was determined for a number of the Examples illustrated above. The results are summarized in the table below.

| Formulation | Dissolution time in SIF, pH 7.5 for 100% release |
|---|---|
| Example 16 85% 4135F, 5% SA, 15% Starch 1500 | 9-16 hrs |
| Example 17 80% 4135F, 5% SA, 10% Starch 1500, 5% lactose | 11-18 hrs |
| Example 18 85% 4135F, 5% SA, 10% Kollidon CL | 3-11 hrs |
| Example 19 80% 4135F, 5% SA, 10% Explotab, 5% lactose | 4-13 hrs |
| Example 21 85% 4135F, 5% SA, 5% NaCl, 5% lactose | 5-18 hrs |
| Example 28 90% 4135F, 5% SA, 5% Pharmacoat 603 | 2-9 hrs |
| Example 29 90% 4135F, 5% SA, 5% lactose | 6-12 hrs |
| Example 10 85% 4135F, 5% SA, 10% lactose | 5-11 hrs |
| Example 11 75% 4135F, 5% SA, 20% lactose | 6-14 hrs |

Dissolution time was conducted on the following E4135/surfactant formulations in a manner similar to that above (USP 3 release profiles) and are summarized in the table below.

| Formulation | Release Time | Variability |
|---|---|---|
| 77% 4135F + 1% SDS + 5% Ac-Di-Sol + 12% stearyl alcohol (SA) + 5% HPMC | 2.5-11 hrs | High |
| 68% 4135F + 15% Ac-Di-Sol + 12% SA + HPMC 5% | 3-7 hrs | High |
| 62% 4135F + 1% SDS +10% Ac-Di-Sol + 10% Explotab + 12% SA + HPMC 5% | 2.5-3.5 hrs | Low |
| 63% 4135F + 10% Ac-Di-Sol + 10% Explotab + 12% SA + HPMC 5% | 5-8.5 | Moderate |
| 52% 4135F + 1% SDS + 15% Ac-Di-Sol + 15% Explotab + 12% SA + HPMC 5% | 3-9 Hours | High |
| 62% 4135F + 1% Pluronic F68 + 20% Explotab + 12% SA + HPMC 5% | 4.5-10 (1 outlier) | Moderate |
| 62% 4135F + 1% Pluronic F127 + 20% Explotab + 12% SA + HPMC 5% | 4-11 | High |

These USP 3 results show that SDS is useful in the 4135F formulation to achieve an early pulse (2.5-3 hours) release. Without SDS, these samples do not detach from the core linker (release appears to occur through small holes at the weld line). Replacing SDS with another surfactant such as Pluronic changes the release time to The USP 3 dissolution profile of a 4135F formulation containing 1% SDS with 10% Ac-Di-sol/10% Explotab was further assessed using a 80% weld intensity to join the linker to the shell. The release profile from these shells was found to be very consistent with release occurring between 2.5-3 hours for all 6 samples tested. These formulations were run again using a weld intensity of 100% to check the variability induced by higher welding intensities. It was determined that the release profile is variable, and release times were spread between 3 and 8 hours, indicating that 80% weld intensity is the optimum.

Characterization of the weld feature and the relevance of welding parameters on dissolution performance have been further investigated on samples consisting of 4135F/20% Explotab/1% SDS/5% Pharmacoat/12% Stearyl alcohol. These samples were embedded in epoxy resin and segmented to examine the weld feature using SEM and optical microscopy. These data indicate that the weld amplitude may significantly affect the weld strength and hence change the dissolution process at the weld feature.

Additional Examples to those above which have been molded but not tested for dissolution characteristics include:
Eudragit 4135F 62%, Stearyl Alcohol (SA) 12%, AcDiSol 5%, Explotab 5%, HPMC 15%, SDS 1%
Eudragit 4135F 42%, SA 12%, AcDiSol 20%, Explotab 20%, HPMC 5%, SDS 1%
Eudragit 4135F 47%, SA 12%, Explotab 10%, HPMC 30%, SDS 1%

Example 30

In accordance with the process described above in Example 1 for the manufacture of pellets, actual (averaged) processing parameters for the following material composition used were:

| Material | % w/w |
|---|---|
| Eudragit 4135F | 75.0 |
| Sodium starch glycollate (Explotab) | 20.0 |
| Stearyl alcohol | 5.0 |

Extruder: PRISM 24 mm twin screw.

| Extrusion conditions (mean): | |
|---|---|
| Extruder screw speed (rpm) | 100 |
| Extruder torque (%) | 52 |
| Extruder pressure (Bar) | 28 |

-continued

| Extrusion conditions (mean): | |
|---|---|
| Feed rate (kg/hour) | 2 |
| Temperature zone 1 (° C.) | 19 |
| Temperature zone 2 (° C.) | 120 |
| Temperature zone 3 (° C.) | 120 |
| Temperature zone 4 (° C.) | 120 |
| Temperature zone 5 (° C.) | 120 |
| Temperature zone 6 (° C.) | 120 |
| Temperature die zone (° C.) | 130. |

Additional formulation examples of the E 4135F polymer as a more delayed release shell component 6-8 hours (late-pulse) which contains an improved hydration response at pH>6 are shown below. In this particular grouping the E4135 is co-blended with hydroxypropylcellulose.

| | #(31) | (32) | (33) | (34) | (35) | (36) | (37) |
|---|---|---|---|---|---|---|---|
| 4135F | 45% | 35% | 25% | 15% | 75% | 65% | 55% |
| Stearyl Alcohol | 10% | 10% | 10% | 10% | 10% | 10% | 10% |
| Lactose | 5% | 5% | 5% | 5% | 5% | 5% | 5% |
| Klucel LF | 40% | 50% | 60% | 70% | 10% | 20% | 30% |
| Total | 100% | 100% | 100% | 100% | 100% | 100% | 100% |

Yet another set of formulations, with the use of a surfactant as a dissolution aid for the E 4135F formulations was prepared using the following blends:

| | (38) | (39) | (40) | (41) | (42) | (43) |
|---|---|---|---|---|---|---|
| 4135F | 63% | 62.9% | 62.75% | 52% | 42% | 62% |
| AcDiSol | 10% | 10% | 10% | 15% | 20% | 5% |
| Explotab | 10% | 10% | 10% | 15% | 20% | 5% |
| Stearyl alcohol | 12% | 12% | 12% | 12% | 12% | 12% |
| Pharmacoat 603 | 5% | 5% | 5% | 5% | 5% | 15% |
| SDS | 0% | 0.1% | 0.25% | 1% | 1% | 1% |

The reproducibility of a formulation, for the early release/pulse component (4135F, 12% stearyl alcohol, 1% SDS and 10/10/5% AcDiSol/Explotab/Pharmacoat 603) has been evaluated in a molding experiment, similar to those indicated above where samples were taken at the start middle and end of a prolonged production run.

Formulations for a delayed release/pulse (6-8 hours) containing a surfactant blend with Eudragit 4135F have also been produced using a APV 19 mm extruder. The following polymer blends were produced:

| | (44) | (45) | (46) | (47) | (48) | (49) | (50) |
|---|---|---|---|---|---|---|---|
| Eudragit 4135F | 57% | 47% | 37% | 57% | 47% | 37% | 75% |
| Stearyl Alcohol | 12% | 12% | 12% | 12% | 12% | 12% | 5% |
| Pharmacoat 603 | 20% | 30% | 40% | — | — | — | — |
| Explotab | 10% | 10% | 10% | 10% | 10% | 10% | 10% |
| Low-Sub HPC | — | — | — | 20% | 30% | 40% | — |
| SLS (Surfactant) | 1% | 1% | 1% | 1% | 1% | 1% | — |
| Lactose monohydrate | — | — | — | — | — | — | 10% |
| Total | 100% | 100% | 100% | 100% | 100% | 100% | 100% |

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. An extruded, injection molded capsule shell comprising a composition comprising:
   a copolymer of methyl acrylate, methyl methacrylate, and methacrylic acid, present in an amount ranging from about 42% to about 72% w/w, with a molar ratio of monomer units of 7:3:1 and a ratio of free carboxyl groups to ester groups of 1:10;
   Stearyl alcohol is present in an amount of about 12% w/w;
   a surfactant selected from the group consisting of sodium dodecyl sulphate and a block copolymer of ethylene oxide and propylene oxide present in an amount ranging from about 0.1% to about 5% w/w;
   a swellable solid present in an amount ranging from about 5% to about 70% w/w selected from the group consisting of, hydroxypropyl cellulose, hydroxypropylmethyl cellulose, hydroxypropylmethyl cellulose phthalate, and combinations thereof; and
   a dissolution modifying excipient present in an amount ranging from about 5% to about 40% w/w selected from the group consisting of sodium starch glycollate, croscarmellose sodium, Lactose, and combinations thereof.

2. The capsule shell according to claim 1, wherein the composition is selected from the group consisting of:

Copolymer 62.9%, Crosscarmellose sodium 10%, Sodium starch glycollate 10%, Stearyl alcohol 12%, Hydroxypropyl methylcellulose 5%, Sodium dodecyl sulphate 0.1%;

Copolymer 62.75%, Crosscarmellose sodium 10%, Sodium starch glycollate 10%, Stearyl alcohol 12%, Hydroxypropyl methylcellulose 5%, Sodium dodecyl sulphate 0.25%;

Copolymer 52%, Crosscarmellose sodium 15%, Sodium starch glycollate 15%, Stearyl alcohol 12%, Hydroxypropyl methylcellulose 5%, Sodium dodecyl sulphate 1%;

Copolymer 42%, Crosscarmellose sodium 20%, Sodium starch glycollate 20%, Stearyl alcohol 12%, Hydroxypropyl methylcellulose 5%, Sodium dodecyl sulphate 1%;

and

Copolymer 62%, Crosscarmellose sodium 5%, Sodium starch glycollate 5%, Stearyl alcohol 12%, Hydroxypropyl methylcellulose 15%, Sodium dodecyl sulphate 1%.

3. The capsule shell according to claim 1, wherein the composition is selected from the group consisting of:

Copolymer 68%, Hydroxypropylmethyl cellulose 10%, Lactose (regular) 5%, Sodium dodecyl sulphate 5%, Stearyl alcohol 12%;

Copolymer 72%, Hydroxypropylmethyl cellulose 10%, Lactose (regular) 5%, Sodium dodecyl sulphate 1%, Stearyl alcohol 12%;

Copolymer 71%, Hydroxypropylmethyl cellulose 10%, Lactose (regular) 5%, Sodium dodecyl sulphate 2%, Stearyl alcohol 12%;

Copolymer 62%, Sodium starch glycollate 20%, Hydroxypropylmethyl cellulose 5%, Sodium dodecyl sulphate 1%, Stearyl alcohol 12%;

Copolymer 62.5%, Sodium starch glycollate 20%, Hydroxypropylmethyl cellulose 5%, Sodium dodecyl sulphate 0.5%, Stearyl alcohol 12%;

Copolymer 62%, Crosscarmellose sodium 10%, Sodium starch glycollate 10%, Hydroxypropylmethyl cellulose 5%, Sodium dodecyl sulphate 1%, Stearyl alcohol 12%;

Copolymer 67%, Crosscarmellose sodium 15%, Hydroxypropylmethyl cellulose 5%, Sodium dodecyl sulphate 1%, Stearyl alcohol 12%;

Copolymer 72%, Crosscarmellose sodium 10%, Hydroxypropylmethyl cellulose 5%, Sodium dodecyl sulphate 1%, Stearyl alcohol 12%;

Copolymer 52%, Crosscarmellose sodium 15%, Sodium starch glycollate 15%, Hydroxypropylmethyl cellulose 5%, Sodium dodecyl sulphate 1%, Stearyl alcohol 12%;

Copolymer 62.9%, Crosscarmellose sodium 10%, Sodium starch glycollate 10%, Hydroxypropylmethyl cellulose 5%, Sodium dodecyl sulphate 0.1%, Stearyl alcohol 12%;

Copolymer 62%, Sodium dodecyl sulphate 1%, Crosscarmellose sodium 10%, Sodium starch glycollate 10%, Stearyl alcohol 12%, Hydroxypropylmethyl cellulose 5%;

Copolymer 52%, Sodium dodecyl sulphate 1%, Crosscarmellose sodium 15%, Sodium starch glycollate 15%, Stearyl alcohol 12%, Hydroxypropylmethyl cellulose 5%;

Copolymer 62%, Polyoxypropylene-polyoxyethylene block copolymer 1%, Sodium starch glycollate 20%, Stearyl alcohol 12%, Hydroxypropylmethyl cellulose 5%;

and

Copolymer 47%, Stearyl alcohol 12%, Sodium starch glycollate 10%, Hydroxypropylmethyl cellulose 30%, Sodium dodecyl sulphate 1%.

4. An extruded, injection molded capsule shell comprising a composition selected from the group consisting of:

Copolymer 62%, Hydroxypropylmethyl cellulose phthalate 20%, Hydroxypropylmethyl cellulose 5%, Sodium dodecyl sulphate 1%, Stearyl alcohol 12%;

Copolymer 77%, Crosscarmellose sodium 5%, Hydroxypropylmethyl cellulose 5%, Sodium dodecyl sulphate 1%, Stearyl alcohol 12%; and Copolymer 63%, Crosscarmellose sodium 10%, Sodium starch glycollate 10%, Hydroxypropylmethyl cellulose 5%, Stearyl alcohol 12%;

wherein the copolymer is a copolymer of methyl acrylate, methyl methacrylate, and methacrylic acid with a molar ratio of monomer units of 7:3:1, and a ratio of free carboxyl groups to esters groups of 1:10.

* * * * *